United States Patent [19]

Koocher

[11] Patent Number: 4,952,513

[45] Date of Patent: Aug. 28, 1990

[54] ASSAYS FOR QUALITATIVE AND QUANTITATIVE DETECTION OF ORGANIC AND INORGANIC ANALYTES OF DIVERSE CHEMICAL CLASSES VIA THE SELECTIVE FORMATION AND GROWTH OF LIGHT SCATTERING CRYSTALS

[75] Inventor: Martin Koocher, Lexington, Mass.

[73] Assignee: Crystal Diagnostics, Inc., Woburn, Mass.

[21] Appl. No.: 261,730

[22] Filed: Oct. 24, 1988

[51] Int. Cl.$^5$ .............................................. G01N 33/00
[52] U.S. Cl. ........................................ 436/36; 436/35;
436/86; 436/20; 436/60; 436/71; 436/73;
436/85; 436/91; 436/100; 436/103; 436/106;
436/119; 436/124; 436/127; 436/139; 436/145;
436/169; 436/182; 436/79; 436/84; 436/111;
436/120; 436/129; 436/131; 436/132; 436/140

[58] Field of Search ..................... 436/20-24,
436/35, 36, 39-42, 60, 61, 63, 64-68, 70-146,
164, 167, 168, 169, 182, 183, 902

[56] References Cited

U.S. PATENT DOCUMENTS 4,380,587  4/1983  Koocher .............................. 436/128
4,816,414  3/1989  Koocher et al. ....................... 436/85

*Primary Examiner*—Robert J. Warden
*Assistant Examiner*—Timothy M. McMahon
*Attorney, Agent, or Firm*—David Prashker

[57] ABSTRACT

The present invention provides a general assay methodology suitable for the detection of organic analytes which are neither aldehydes nor ketones and for inorganic substances. The methodology utilizes prepared sensitized films of derivatizing agents and specific developer solutions for the selective and controlled formation of light scattering crystals whose presence serves as a qualitative and/or quantitative measure of the individual analyte of interest in the sample.

20 Claims, No Drawings

ASSAYS FOR QUALITATIVE AND QUANTITATIVE DETECTION OF ORGANIC AND INORGANIC ANALYTES OF DIVERSE CHEMICAL CLASSES VIA THE SELECTIVE FORMATION AND GROWTH OF LIGHT SCATTERING CRYSTALS

FIELD OF THE INVENTION

The present invention is concerned generally with assays for the qualitative and quantitative detection of individual organic and inorganic analytes of interest drawn generally from the diversity of chemical classes presently known; and is particularly directed to methods and sensitized films for the specific detection of individual organic and inorganic analytes by the selective formation and growth of light scattering crystals.

BACKGROUND OF THE INVENTION

As traditionally viewed in the scientific literature, a crystal is a solid in which the constituent atoms or molecules are arranged in a regular, repeating pattern. The repeating units, often termed "unit cells", are identical parallelopipeds stacked in a space-filling array. The vertices of the unit cells are referred to as the crystal lattice or space lattice. The lattice points are occupied by identical ions, atoms, or molecules. In body-centered crystal structures there is by definition another ion, atom, or molecule at the center of each unit cell which may be different from the ones at the lattice points. Alternatively, in face-centered crystal structures, there is an atom or molecule at the center of each face of the unit cell.

All true solids regardless of chemical composition are crystalline in the pure state—that is, they are structurally a lattice of repeating crystal unit cells. Alternatively, amorphous solids such as glasses, resins, and polymers are actually high-viscosity, supercooled fluids that undergo a very slow plastic flow. Chemically, the ability to obtain any given substance in crystalline form is to a large extent a measure of its purity; and this has provided a now classical means for its identification. Methods of qualitative analysis were developed in the 18th and 19th centuries for identification of a given composition by the ability to crystallize it; and subsequently to identify the substance by its melting point and refractive index. The microscope was first used in analyis by F. V. Raspail [*Noureau System de Chimie Organique Fonde Sur Des Methodes d'Observation*, Paris, 1833] who used the crystal habit of a solid as a means of identifying chemical compounds. This pioneer work led others to utilize chemical microscopy as a method of identifying crystalline solids. Such methods have long since become standardized procedures [Cheronis and Entrikin, Systematic Semi-Micro Qualitative Organic Analysis, 2nd edition, 1947]; and standard handbooks of physics and chemistry commonly provide page after page of chemical compositions and formulas, each of which has been identified and evaluated by its crystalline melting point and crystalline refractive index as a basis for their individual identity [*Handbook Of Chemistry And Physics*, 56th edition, CRC publications, 1975-1976]. On this basis also, investigative efforts have been made regarding reactions and methods for preparing many different chemical compositions in crystalline form. Such investigations have included: examination of the various crystal systems and crystalline structures which could exist; means of inducing crystal formation; and methods for obtaining different chemical formula and structure in a crystalline state. Representative of these investigative efforts are the individual texts and reviews in: *Industrial Engineering Chemistry*, volume 61, pages 65-101, 1969, and volume 62, pages 148-155, 1970; Cheronis and Entrikin, *Identification Of Organic Compounds*, 1963; Cheronis, Entrikin, and Hodnett, *Semi-Micro Qualitative Organic Analysis*, 3rd edition, 1965; Koler, L. and Kofler, A., *Mikromeihoden Zur Kennzeichnung Organische Stoffe U Stoffgemische*, Innsbruck, 1948; Shriner, Fusow, and Curtin, *The Systemic Identification Of Organic Compounds*. 4th edition, 1956; Behren's-Kley, *Organische Mikrochemische Analysis* (translated, Richard E. Sterens), Microscope publications Ltd, 1969.

Only recently has there been any major deviation from the traditional means for identifying crystalline substances via their physical properties of melting point; refractive index; or crystalline shape, habit, and appearance under the microscope. These innovations have taken the form of assays for the specific detection of carbonyl-containing compounds by the controlled and selective formation of light scattering crystals. These assays are described within U.S. Pat. Nos. 4,380,587 and 4,727,024 respectively. The procedures described within these patents are able to detect aldehydes and ketones exclusively (the carbonyl-containing compounds) by a series of selective chemical reactions which result in the formation of optically detectable crystals as the basis for determining the presence or absence of a carbonyl-containing compound in a test sample. As advantageous as these innovations are within qualitative and quantitative detection assays, they are limited exclusively to the detection of carbonyl-containing compounds—that is, only the detection of aldehydes and ketones as a chemical class. These methods are unsuitable and ineffective for the detection of any other organic analyte of interest; and are equally inappropriate and inoperative for the detection of inorganic analytes under any circumstances. The growing recognition and value of the methods described within these patents has emphasized the continuing absence of accurate and reliable methods for the selective detection of other organic and inorganic substances via the selective formation and growth of light scattering crystals; and has focused the attention of the ordinary practitioner in this art on the many advantages and benefits provided by such analytical assays were such detection methods able to be created and designed in a reproducible and accurate manner. Insofar as is presently known, however, there has been no innovation or expansion upon the self-limiting assay procedures as described.

SUMMARY OF THE INVENTION

The present invention provides unique, general assay methods for the detection of individual organic and inorganic analytes of interest via the selective formation and growth of light scattering crystals. The present invention provides a method for selectively detecting an organic analyte of interest which is neither an aldehyde nor a ketone, this method comprising the steps of:

obtaining a fluid believed to contain the organic analyte of interest, the organic analyte being devoid of carbonyl groups and comprising at least one identifying reactive entity whose chemical composition and structure identifies the organic analyte as being of a specific chemical class;

exposing the organic analyte of interest in the fluid to a derivatizing agent selectively reactive with the identifying chemical entity of the organic analyte to yield a reaction product formed in-situ as a plurality of immobilized, nucleating sites;

treating the immobilized, nucleating sites with a metastable supersaturated solution comprising a substance which is at least an analogue of the reaction product yielded by the derivatizing agent and the organic analyte such that a plurality of optically detectable crystals are formed; and detecting the presence of the formed crystals as a measure of the analyte of interest in the fluid.

The invention also provides a method for selectively detecting an inorganic analyte of interest, this method comprising the steps of:

obtaining a fluid believed to contain the inorganic analyte of interest, the inorganic analyte comprising an identifying reactive entity whose chemical composition and structure identify the inorganic analyte as being of a specific chemical class;

exposing the inorganic analyte of interest in the fluid to a derivatizing agent selectively reactive with the inorganic analyte to yield a reaction product formed in-situ as a plurality of immobilized nucleating sites;

treating the immobilized nucleating sites with a metastable supersaturated solution comprising a substance which is at least an analogue of the reaction product yielded by the derivatizing agent and the inorganic analyte such that a plurality of optically detectable crystals are formed; and detectinq the presence of the formed crystals as a measure of the inorganic analyte of interest in the fluid.

The present invention also provides a variety of different sensitized films and test apparatus for performing the diverse methods. The use of such prepared sensitized films and apparatus maximizes the speed, accuracy, and precision of the reactions for greatest efficacy and use.

DETAILED DESCRIPTION OF THE PREFERRED EMBODIMENTS

The present invention is a generally useful assay methodology for the direct detection of an organic analyte of interest which is neither an aldehyde nor a ketone; and for the direct detection of an inorganic analyte of interest in a gaseous or liquid sample. The assay methodology may be performed in a qualitative or quantitative manner using a noninstrument device, typically a portable device containing a sensitized film, which exposes the analyte of interest to the requisite reactants in the proper sequence for selective reactive formation and growth of optically detectable light scattering crystals on a solid substrate. The innovations and improvements provided by the unique methodology and apparatus allows direct detection of individual organic and/or inorganic analytes of interest to be detected without conversion into a carbonyl ($>C=0$) containing composition at any time; and provides accurate, reproducible, and reliable assays for the detection of a wide variety of chemically different, hazardous, and/or toxic substances.

This assay methodology utilizes carefully prepared sensitized films that react specifically and sensitively with a wide variety of individual analytes to produce a singular derivatized reaction product on the film surface that, in most cases, is invisible to the unaided eye and is, thus, comparable to the "latent image" produced in conventional photography. This invisible "latent image" is then made visible to the unaided eye by treating the analyte-exposed, sensitized film with a developer comprising a metastable supersaturated solution of the derivatized analyte. As shown below, this assay methodology has many similarities to and parallels with photography.

| ASSAY METHODOLOGY | PHOTOGRAPHY |
|---|---|
| 1. Utilizes a sensitized film | Utilizes a sensitized film |
| 2. Different films used with different analytes | Different films used with different types of radiation (light) |
| 3. Exposure of film to analyte produces invisible latent image | Exposure of film to radiation (light) produces invisible latent image |
| 4. Latent image made visible by crystal growth developer | Latent image made visible by photographic developer |

It will be appreciated also that a major operating principle of apparatus containing such a sensitized film is based upon "Fick's First Law of Diffusion" for sampling gases and utilizes nucleation and crystal growth for analysis. After activation of the sensitized film within the badge, the analyte of interest preferably is allowed to passively diffuse as a gas over the film surface at a rate determined by Fick's law; and to react with the sensitized film to form a "latent image" consisting of submicroscopic crystal nuclei. Afterwards, a developing solution is applied over the exposed film which causes the previously invisible crystals to grow into visible size. After a few minutes, a developed line appears, the length of which is proportional to the concentration of the analyte in the sample. The concentration of analyte is determined from a calibration chart which converts the line length (typically in millimeters) as a function of sampling period to a time-weighted-average measurement.

The present assay methodology is thus unique and provides major advances over even other recently developed assay methods and apparatus which rely upon the formation and growth of optically visible, light scattering crystals as the means for making quantitative and qualitative determinations. The present assay methodologies alone are based and rely upon direct reaction of the specific analyte of interest with a selective derivatizing agent—without prior existence as or conversion of the analyte into an entity containing a reactive carbonyl-containing compound. While it is recognized that sometimes a chemical composition can be structurally synthesized to contain a carbonyl group ($>C=0$) in a hidden or protected manner which prevents the carbonyl group from being chemically reactive, this is generally not the case. Accordingly, the organic analytes detectable by the present invention are each individually devoid of chemically reactive carbonyl groups; and it is an essential feature of the present invention that the organic analyte to be detected be maintained in a physical and chemical state which completely avoids the formation, addition, or introduction of reactive carbonyl-containing groups at all times. Similarly, when the present methodology is employed for detection of an inorganic analyte of interest, the requirement of being devoid of reactive carbonyl groups is met by definition and by the nature of its being an inorganic substance. The present invention is thus substantially and distinctly different from the methods described within U.S. Pat. Nos. 4,380,587 and 4,727,024, each of which demands the presence of a pre-existing carbonyl-containing analyte. Similarly, U.S. Ser. No. 105,138, filed Oct. 2, 1987, describes and claims methods and apparatus for detecting an analyte of interest capable of being converted into a carbonyl-containing composition; and thus is substantially different and distinct from the assay methodology of the present invention.

The practitioner ordinarily skilled in this art will recognize and appreciate that the present assay methodology and apparatus provides a number of major benefits and advantages to the user. These include:

(1) The assay methodology and apparatus offers the selective capability for detecting specific chemical entities not only among the many organic, and/or classes, and/or families and inorganic orders of compositions and functional groups; but also among the individual members within any single chemical category desired with precision and accuracy.

(2) The assay methodology and apparatus is able to selectively detect a single organic or inorganic analyte of interest so long as the analyte comprises at least one "identifying reactive entity" whose chemical composition and structure serves as the means for identifying the analyte as being of or within a specific chemical class. Such selective detection can be made regardless of whether the analyte of interest is alone or is in admixture within the fluid sample presented for analysis.

(3) The assay methodology and apparatus provides for qualitative and/or quantitative measurements as required or desired without need of any instrumentation whatsoever; and yet is able to provide rapid, easily obtained, and consistently reliable results and data.

(4) The assay methodology and apparatus can directly detect a single analyte of interest in a fluid sample; and does not require either pretreatment or fractionation of the fluid sample to exclude other compositions within or outside the chemical class of the analyte prior to performing the steps of the methodology.

(5) The assay methodology and apparatus has broad applications and may be employed within environmental, biochemical, analytical, and clinical/diagnostic test areas generally without restriction.

(6) The assay methodology can be performed using a prepared sensitized film and badge device which is portable, disposable, and enables the assay to be performed anywhere on-site in the field, at any time as needed or desired by the user.

(7) Finally, the assay methodology and apparatus of the present invention can be utilized effectively by the untrained layman without prior technical education or experience in chemical reaction systems.

In order to more easily and fully understand the apparatus and each of the assay methods provided by the present invention, a broad, general disclosure of each manipulative step and of each discrete reactant employed within the assay methodologies is provided initially. This broad, general disclosure will then be followed in text by a series of individual detailed descriptions for specific classes of organic and inorganic analytes which cumulatively are representative and illustrative of the overall diversity and extensive range of applications for the present invention. By proceeding in this manner, the many distinguishing features of the individual reactions and the major advantages of the present assay methodology and apparatus as a whole will become apparent.

CHEMICAL COMPONENTS AND METHOD GENERALLY

The Analyte Of Interest And The "Identifying Reactive Entity"

The assay methodology of the present invention is an all-encompassing procedure employed to selectively detect and to qualitatively and quantitatively measure a wide range of organic and inorganic analytes of interest generally. There are only three limitations and restrictions regarding the analyte of interest to be detected. First, it is required that the analyte of interest not utilize a carbonyl group as an identifying reactive entity at any time during the assay protocol. This requirement pertains to organic analytes exclusively in that every inorganic analyte is by definition and nature devoid of reactive carbonyl groups inherently. It will be noted also that by definition and convention carbon monoxide, carbon dioxide, and carbonate ions are considered not to contain a carbonyl group as a functional chemical moiety. This first requirement is sufficiently broad to also demand that the analyte of interest to be detected avoid utilizing a carbonyl group as the identifying reactive entity not only initially—but also requires that the analyte avoid being converted into a composition having a reactive carbonyl group as part of its formula and structure at any time during the performance of the assay methodology.

The second requirement for each and every analyte of interest to be selectively detected using the present assay methodology is that the individual analyte comprise at least one "identifying reactive entity" whose chemical composition and overall structure identifies the analyte as the specific substance to be detected. The term "identifying reactive entity" as used herein is therefore employed most broadly and encompasses by definition the chemical compositions and structures present in at least five different chemical formats. Representative examples of an "identifying reactive entity" and of the five different chemical formats are provided by Tables I and II respectively below. In each instance, however, the "identifying reactive entity" is a discrete molecule, moiety, functional group, atomic element, or compound—whose presence and specific reactivity alone serve as an identifying label, property, or characteristic by which the analyte of interest is detected and distinguished from other chemical compositions and substances.

TABLE I

| CLASS NAME | IDENTIFYING REACTIVE ENTITY |
|---|---|
| A. NITROGENOUS BASES | |
| Primary Amines | $RNH_2$, $ArNH_2$ |
| Secondary Amines | $RR'NH$, $Ar_2NH$, $ArNHR$ |
| Tertiary Amines | $RR'R''N$, $Ar_3N$ |
| Hydrazines | $-NHNH_2$ |
| Hydrazides | $-CONHNH_2$ |
| B. ALIPHATIC ALCOHOLS | |
| Primary | $R-\underset{\underset{H}{\vert}}{\overset{\overset{H}{\vert}}{C}}-OH$ |
| Secondary | $R-\underset{\underset{R'}{\vert}}{\overset{\overset{H}{\vert}}{C}}-OH$ |

TABLE I-continued

| CLASS NAME | IDENTIFYING REACTIVE ENTITY |
|---|---|
| Tertiary | $R-\underset{\underset{R'}{|}}{\overset{\overset{R''}{|}}{C}}-OH$ |
| C. PHENOLS | ArOH |
| D. ORGANIC ALKYL HALIDES | $R-Cl, R-Br, R-I, R-F$ |
| E. CARBOXYLIC AND SULFONIC ACIDS | $-COOH$ and $-SO_3H$ |
| F. THIOLS AND MERCAPTANS | $-SH$ |
| G. HYDROCARBONS | |
| aromatic | ArH |
| aliphatic | RH | wherein R, R', and R" are alkyl moieties; and Ar is an aryl moiety.

TABLE II

| CLASS NAME | IDENTIFYING REACTIVE ENTITY | |
|---|---|---|
| AA'. ALKALI METAL CATIONS | | |
| sodium | $Na^+$ | |
| potassium | $K^+$ | |
| lithium | $Li^+$ | Monovalent Cations |
| cesium | $Cs^+$ | |
| ammonium | $NH_4^+$ | |
| BB'. ALKALINE EARTH METAL CATIONS | | |
| calcium | $Ca^{++}$ | |
| strontium | $Sr^{++}$ | Divalent Cations |
| barium | $Ba^{++}$ | |
| magnesium | $Mg^{++}$ | |
| CC'. TRANSITION NOBLE METAL CATIONS | | |
| silver | $Ag^+$ | |
| mercuric | $Hg^{++}$ | |
| platinum | $Pt^{+++}$ | |
| gold | $Au^{+++}$ | |
| palladium | $Pd^{++++}$ | |
| DD'. TRANSITION METAL CATIONS | | |
| tin (stannous) | $SN^{++}$ | |
| lead | $Pb^{++}$ | |
| copper | $Cu^{++}$ | |
| zinc | $Zn^{++}$ | |
| cadmium | $Cd^{++}$ | |
| EE'. INORGANIC HALIDE ANIONS | | |
| fluoride | $F^-$ | |
| chloride | $Cl^-$ | Monovalent Anions |
| bromide | $Br^-$ | |
| iodide | $I^-$ | |
| FF'. HALOGENS | | |
| fluorine | $F_2$ | |
| chlorine | $Cl_2$ | |
| bromine | $Br_2$ | |
| iodine | $I_2$ | |
| GG'. SULFUR ANIONS | | |
| sulfide | $S^=$ | |
| sulfite | $SO_3^=$ | Divalent Anions |
| sulfate | $SO_4^=$ | |
| HH'. PHOSPHOROUS RADICAL ANIONS | | |
| metaphosphate | $PO_3^-$ | |
| tribasic (ortho) phosphate | $PO_4^{32}$ | |

The third and last requirement is that the analyte of interest present the identifying reactive entity for specific reaction with a pre-chosen derivatizing agent (typically immobilized on a solid substrate as a sensitized film) to produce a plurality of nucleating sites in-situ which are immobilized on the surface of the substrate. The nucleating sites formed in-situ are submicroscopic-sized crystal nuclei immobilized on the surface of the solid substrate; and represent the "latent image" to be developed subsequently as a crystalline layer of optically visible crystals. A major part of the present invention thus depends upon the ability of having the identifying reactive entity of the analyte act to selectively combine and react with the chosen derivatizing agent; and upon the resulting reaction product (regardless of true chemical composition) taking physical form in-situ as a series of submicroscopic-sized crystal deposits which are immobilized on the surface of the supporting film.

As will be appreciated by a careful examination and review, Tables I and II divide all analytes generally into two Orders: organic compositions and inorganic compositions. The Order of organic compositions described by Table I inherently includes the two families of aliphatic and aromatic organic compositions; and is subdivided further into individual chemical classes, each of which is based upon and illustrates one identifying reactive entity which can be differentiated and distinguished from the others. Table I provides a symbolic notation whenever possible for the specific chemical format and structure which is the identifying reactive entity by which that class of chemical composition and structure is identified. Table I provides examples of only two of the five different chemical formats useful as an identifying reactive entity. One format is the traditional functional group which is a constituent moiety of the analyte as a whole and provides the selective reactive characteristics for the analyte by its very presence. Examples are: the various nitrogen based function groups; the hydroxyl groups of alcohols and phenols; the halide atom attached to an alkyl or aryl moiety; and the carboxylic group of the organic acids.

The second chemical format for the identifying reactive entity is exemplified by the class of (aromatic and aliphatic) hydrocarbons—in which it is the chemical composition and structure of the entire molecule as a discrete whole which provides the identifying reactive characteristics of the class. In this format, it is the entire molecular structure of the analyte which is the "identifying chemical entity" rather than any one or more component parts of the composition which identities each member as being within a single chemical class.

The other three chemical formats are represented and illustrated by the chemical classes listed within Table II. It will be noted that the Order of inorganic compositions also is inherently subdivided into the Family of inorganic atomic elements of the Periodic Table and the Family of inorganic radicals and compounds as these have been differentiated in this art. These Families have themselves been broken into specific chemical classes whose membership provides a recognizable and reliable basis for their grouping. The classes of Table II illustrate and provide the other chemical formats encompassed within the term "identifying chemical entity". Accordingly, it will be recognized that such classes as the sulfite, sulfate, and the phosphorous containing anions represent inorganic compounds in ionized radical group form; a format whose chemical composition and structure identify them and distinguish them from other inorganic organizational forms. Alternatively, the chemical classes of alkaline earth metals, the transition metals, and the inorganic halides each are examples of atomic elements which are detectable as ionized atoms rather than in radical or compounded form. The atomic elemental format is the fourth type of identifying reactive entity possible. The fifth type of format is represented by the halogen class of Table II. In contrast to halides which are by definition compounded with other substances and detected in their anionic form, the halogens are neutral, non-ionic elemental atoms present in a true molecular state. The neutral molecular state for the atomic element serves as the fifth form of identifying reactive entity. All of these chemical formats are within the scope of the present invention.

It is also possible that in a very limited number of instances, the individual analyte of interest initially will not contain or present at least one identifying reactive entity and whose chemical composition and structure will not serve to identify the analyte in its original state as being of a specific chemical class. These limited situations and circumstances are expected to pertain to organic analytes predominantly in view of the almost limitless variety of chemical formulations and structures presently known not withstanding those compositions and structures yet to be discovered or synthesized. For this reason, it is expected and desired that if an analyte of interest in its original state should not provide an identifying reactive entity representative of a specific chemical class, it is intended that the analyte be reacted with a ligand comprising at least on identifying reactive entity in order to form a hybrid reaction product. It is essential that this hybrid reaction product retain the identifying, reactive entity after its production; and that the hybrid reaction product act as a substitute for the original analyte of interest in all subsequent reactions performed in accordance with the assay methodology of the present invention. It must be understood and emphasized, however, that this additional procedure of artificially adding at least one identifying, reactive entity is necessary only in those few instances where the true analyte of interest in its original state is unable to provide chemical evidence of being categorized within a specific chemical class. Under all other assay circumstances, the analyte of interest in its original and intact natural state should be employed directly as a discrete entity.

The Fluid Sample Containing The Analyte Of Interest

It is intended that the unique assay methodology and apparatus of the present invention utilize any fluid sample obtained from any source of origin believed to actually contain or supply the analyte of interest. Moreover, because diverse applications of the assay methodology are expected within different fields of technology, it is expected that the sample if solid will be prepared in liquid or gaseous form; and that the sample will be obtained from or correlated to those sources whose existance and value is substantially affected by the presence or absence of the individual analyte of interest. Accordingly, if the application of the present methodology is within a diagnostic/clinical setting, it is expected that the fluid sample will come from humans or animals who are suspected of being afflicted with a disease or disorder yet to be identified. Thus the sample can take the form of blood, plasma, serum, urine, lymph, cerebrospinal fluid, gastric juices, and any other liquid or semi-solid specimen from a living subject. Alternatively, should the application be environmental evaluations or assays, the fluid sample will likely include potable waters, wastewaters, industrial discharge fluids, sewage waters, and waters taken from rivers, lakes, and streams. The possible environmental applications also deemed to include evaluation and monitoring of the ambient air or other gaseous environments at home or in the work place. In addition, should the application be chemical or biochemical in nature, the fluid sample will typically take the form of specifically prepared solutions, dispersions, colloids, and other liquid mixtures; as well as gaseous mixtures comprising the analyte of interest and at least one fluid gaseous carrier. Clearly, the nature of the fluid sample containing the analyte of interest will vary with the nature, source, and application for the assay methodology. Accordingly, the composition and source of the fluid sample is immaterial to the present invention so long as these do not substantially interfere with the requisite chemical reactions and the sequence of manipulative steps comprising the present assay methodology.

The Selective Derivatizing Agent

The derivatizing agent is a predetermined chemical composition which is selectively reactive with the identifying chemical entity indicative of a specific chemical class such that a reaction product is formed in-situ on the sensitized film as a plurality of immobilized nucleating sites. Since each specific chemical class has one individual identifying reactive entity of unique chemical composition and structure, it is clear that a variety of different categories of selective derivatizing agents are available, each of which optimally discriminates among the various chemical classes and is selectively reactive with only one identifying chemical entity representative of a single chemical class. Once in reactive contact with the analyte of interest comprising the specific identifying reactive entity, the selective reaction yields a condensation product formed as a plurality of submicroscopic nucleating sites in-situ. To achieve this purpose, the chosen derivatizing agent has been previously deposited onto the surface of a solid substrate to form a sensitized film; and, after selective reaction with the analyte of interest presenting the proper identifying reactive entity, to provide thereby a series of immobilized nucleating sites formed in-situ for the subsequent formation and growth of optically visible crystals.

On this basis, therefore, it is clear that each chemical class of analytes to be detected is correlated and desirably combined with an individual category of derivatizing agents whose membership is selectively reactive with the identifying reactive entity of the analyte to yield a reaction product formed in-situ as a plurality of immobilized nucleating sites. A representative listing of derivatizing agent categories selective for each chemical class is provided by Tables III and IV respectively below.

TABLE III

| CLASS NAME | PREFERRED DERIVATIZING AGENT | COMPOSITION OF PREFERRED DERIVATIZED PRODUCT AND DEVELOPER SOLUTION |
|---|---|---|
| A. NITROGENOUS BASES | — | |
| primary amines | aryl aldehydes | aryl imines (Schiff's bases) |
| secondary amines | aryl acids | aryl acid salts |
| tertiary amines | sodium tetraphenyl boron | sodium tetraphenyl borate salts |
| hydrazines | aryl aldehydes | aryl imines (Schiff's bases) |
| hydrazides | aryl aldehydes | aryl imines (Schiff's bases) |
| B. ALCOHOLS | | |

TABLE III-continued

| CLASS NAME | PREFERRED DERIVATIZING AGENT | COMPOSITION OF PREFERRED DERIVATIZED PRODUCT AND DEVELOPER SOLUTION |
|---|---|---|
| primary | pseudosaccharin chloride | pseudosaccarin ethers |
| secondary | aryl isocyanates | aryl urethanes |
| tertiary | aryl acid chlorides | aryl esters |
| C. PHENOLS | aryl nitro acid chlorides | aryl nitro esters |
|  | aryl nitro halides | aryl nitro ethers |
| D. ORGANIC ALKYL HALIDES | 6-nitro-2-mercapto benzothiazole | 2,2'-(alkylene),bis (6 nitrobenzothiazoles) |
| E. ORGANIC ACIDS |  |  |
| carboxylic acids | 5-benzylthiuronium chloride | 5-benzylthiuronium carboxylates |
| sulfonic acids | aryl amines | aryl amine sulfonates |
| F. THIOLS AND MERCAPTANS | mercuric chloride | mercuric mercaptans |
| G. HYDROCARBONS |  |  |
| aromatic | 2,4,7-trinitro-fluorenone | aromatic hydrocarbon-2,4,7-trinitrofluorenone addition products |
| aliphatic | thiourea | aliphatic hydrocarbon thiourea adducts |

TABLE IV

| CLASS NAME | PREFERRED DERIVATIZING AGENT | COMPOSITION OF PREFERRED DERIVATIZED PRODUCT AND DEVELOPER SOLUTION |
|---|---|---|
| AA' ALKALI METAL CATIONS |  |  |
| sodium | zinc uranyl acetate | sodium zinc uranyl acetate |
| potassium | sodium tetraphenyl boron | potassium tetraphenyl borate |
| lithium | ferric periodate | lithium ferric periodate |
| cesium | sodium tetraphenyl boron | cesium tetraphenyl borate |
| ammonium | sodium tetraphenyl boron | ammonium tetrapheny borate |
| BB' ALKALINE EARTH METAL CATIONS |  |  |
| calcium | sodium oxalate | calcium oxalate |
| strontium | sodium rhodizonate | strontium rhodizoate |
| barium | sodium rhodizonate | barium rhodizonate |
| magnesium | potassium oxalate | magnesium oxalate |
| CC' NOBEL METAL CATIONS |  |  |
| silver | potassium iodide | silver iodide |
| mercuric | potassium iodide | mercuric iodide |
| platinum | p-dimethylamino benzylidene rhodanine | platinum p-dimethyl-amino benzylidene rhodanine |
| gold | p-dimethylamino benzylidene rhodanine | gold p-dimethyl-amino benzylidene rhodanine |
| palladium | p-dimethylamino benzylidene rhodanine | palladium p-dimethyl-amino benzylidene rhodanine |
| DD' TRANSITION METALS |  |  |
| tin (stannous) | potassium oxalate | stannous oxalate |
| lead | potassium chromate | lead chromate |
| copper | quinaldinic acid | copper quinaldinate |
| zinc | quinaldinic acid | zinc quinaldinate |
| cadmium | potassium oxalate | cadmium oxalate |
| EE' INORGANIC HALIDE ANIONS |  |  |
| fluoride | silver nitrate | silver fluoride |
| chloride | silver nitrate | silver chloride |
| bromide | silver nitrate | silver bromide |
| iodide | lead nitrate | lead iodide |
| FF' MOLECULAR HALOGENS |  |  |
| fluorine | maleic acid | 2,3-difluoro-succinic acid |
| chlorine | fumaric acid | 2,3-dichloro-succinic acid |
| bromine | fumaric acid | 2,3-dibromo-succinic acid |
| iodine | maleic acid | 2,3-diiodo-succinic acid |
| GG' SULFUR ANIONS |  |  |
| sulfides | lead nitrate | lead sulfide |
| sulfite | copper sulfate | copper (cupric) sulfite |
| sulfate | barium nitrate | barium sulfate |
| HH' PHOSPHOROUS RADICAL ANIONS |  |  |
| metaphosphate | calcium nitrate | calcium metaphosphate |
| tribasic (ortho) phosphate | calcium nitrate | calcium (ortho) phosphate |

It will be appreciated that each chemical class has been correlated with an individual category of preferred derivatizing agents that can be used in the manufacture of a suitable sensitized film; and that the membership of each individual category typically comprises several different types of derivatizing agents, each type providing a group of discrete chemical reactants which are individually useful. It will be appreciated also that Tables III and IV respectively provide identification of the reaction product formed in-situ on the surface of the film after an analyte of interest of that specific chemical class is combined with one or more selectively reactive derivatizing agents useful for this purpose.

It will be recognized and appreciated that by carefully choosing the membership for each category of derivatizing agents, several bases and means for controlling the specificity, accuracy, and reproducibility of the present invention as a whole are provided. Specificity and assay precision are provided by the individual category of derivatizing agent which is by definition selectively reactive with the identifying reactive entity of a single chemical class. A second basis for control and specificity resides in the individual types of compositions within a single category of derivatizing agent. For example, as regards the chemical class of nitrogenous bases, three different types of derivatizing agents are preferred: sodium tetraphenyl boron; aryl aldehydes; and aryl acids. When an analyte of interest comprising a nitrogen containing base moiety is combined with each type of agent within this category, a variety of different reaction products are formed, each representative of that general type of reaction. Clearly, aryl imines are different and distinguishable from aryl amine salts; each of which in turn is different and distinguishable from sodium tetraphenyl borate salts. Clearly, therefore, the unique composition of each individual reaction product formed provides a second major basis for specific detection and control for the methodology as a whole. A third major level of specificity and control for the invention is provided by the the exact composition of the developer solution, the details of which are described hereinafter.

Each of the individual derivatizing agents used in the present invention, regardless of category or type, preferrably is employed as a dispersion of particles substantially of the same size which are retained on the surface of a solid substrate with relatively uniform spacing between them, the particles preferably ranging from about 0.1–1.0 micrometers in size. The prepared article is a sensitized film to be positioned within a badge or similar apparatus. It is intended that each derivatizing agent, regardless of category or type, be useful for reaction with the desired analyte of interest presenting an identifying reactive entity representative of a specific chemical class regardless of whether the analyte appears in a vaporized or liquid physical state. Each derivatizing agent will selectively react with the identifying reactive entity of the analyte of interest to form a plurality of immobilized nucleating sites in-situ on the surface of the solid substrate. It will be understood that the nucleating sites formed in-situ are themselves submicroscopic-sized crYstals which are invisible to the unaided eye (i.e., the "latent image") but which serve as specific initiation sites for the subsequent formation and growth of optically detectable crystals.

A sensitized film of monodispersed particles comprising the chosen derivatizing agent may be conveniently prepared by directing an aerosol of the solution comprising the derivatizing agent of choice against the surface of a solid substrate in a conventionally known manner. By maintaining very accurate control over the concentration of derivatizing agent in the aerosol and by controlling the speed of delivery of the aerosol to the surface of the solid substrate, one may deposit accurately a controlled amount of the derivatizing agent onto the surface as a discrete sensitized film. To obtain satisfactory adherence of the aerosol particles to the surface of the solid substrate, it is often desireable (but not necessary) to pretreat the substrate surface by application of an electrostatic charge and/or by heating the aerosol. Equipment for forming the aerosol in the desired range of particles is commercially available.

It should be noted also that the solid substrate upon which the chosen derivatizing agent is deposited may be shaped into a variety of different dimensions and configurations. The preferred shapes and sizes for the sensitized film and the preferred apparatus for practicing the methodology has been in great detail previously within U.S. Pat. Nos. 4,380,587 and 4,727,024, the texts of which are expressly incorporated by reference herein Such apparatus provides a variety of differently configured portable badges and similar devices which may be prepared as articles which utilize the methodology of the present invention in the described manner. For this reason, no further descriptive details of the apparatus and articles disclosed within these issued patents are provided herein. The membership of each category and type of derivatizing agent as described herein may be employed within these articles and apparatus for the purpose of forming a plurality of immobilized nucleating sites in-situ and subsequently developing them into optically visible crystals.

The Metastable Supersaturated Developer Solution

Supersaturation plays a vital role in the crystallization process, and Ostwald (1897) and Miers (1906) suggested that two types of supersaturation could be recognized; namely, the metastable and labile states, respectively. They defined the states of supersaturated in the following manner: (1) the stable (unsaturated) state where crystallization is impossible; (2) the metastable (supersaturated) state, where spontaneous nucleation is improbable (although a crystal located in a metastable solution would grow); and (3) the unstable or labile (supersaturated) state where spontaneous nucleation is probable but not inevitable. It is always the metastable supersaturated state which is employed for use within the present invention as the developer solution.

Once the immobilized nucleating sites have been formed in-situ on the surface of a solid substrate via the reaction of the analyte of interest with the selective derivatizing agent, the material of the nucleating sites are preferably treated with a carefully chosen metastable supersaturated developer solution such that a plurality of optically detectable crystals are selectively formed on the surface of the solid substrate. The developer solution is an aqueous or non-aqueous liquid containing a supersaturated concentration of a crystal growing substance which is both chemically and physically stable for a defined period of time; and comprises a substance which in most instances is chemically identical to the material comprising the individual nucleating sites, but in some case is but an analogue of the product yielded by the reaction of the individual derivatizing agent with the analyte of interest. The term "analogue" as employed in this context is defined in the conventional manner and identifies a substance which is substantially similar but not identical to the chemical composition and structure of the reaction product formed by the combination of the individual derivatizing agent and the analyte of interest.

Accordingly, when the metastable supersaturated developer solution is combined with the immobilized nucleating sites formed in-situ on the surface of the solid substrate, crystallization will occur at each of the individual nucleating sites resulting in the formation and growth of light scattering crystals optically detectable by the unaided eye. A useful, but non-exhaustive listing of substances which can be prepared as selective metastable supersaturated developer solutions is provided broadly by Tables III and IV respectively for each specific chemical class. The quantities of each substance and the manner of utilizing each particular composition to prepare a metastable supersaturated developer solution in aqueous and non-aqueous liquids are conventionally known in the art.

It will be noted and appreciated that the listing of developer solutions provided by Tables III and IV respectively indicate that the composition of the metastable supersaturated developer solution is preferably identical to the condensation reaction product formed by the reaction of the individual derivatizing agent with the analyte of interest in each instance. It is especially emphasized, however, that under alternative circumstances, the chemical composition of the metastable supersaturated developer solution need not be chemically identical to the condensation product forming the individual nucleating sites, but may be merely analogous in chemical formula and structure; a condition which is sufficiently similar for crystallization to occur. This is a phenomenon termed "epitaxy". For purposes of the present invention, it is preferred that the chemical composition and structure of the substance used as the metastable supersaturated developer solution be identical to the chemical composition of the condensation product forming the individual nucleating sites on the solid substrate in order to provide the third level of selectivity and control by which to distinguish an individual analyte of interest from a closely similar, analogous ligand. When there is exact chemical identity between the nucleating site material and the developer solution, a third major basis of selectivity and control is created and exercised such that substances closely analogous and/or homologous to the analyte may be individually detected and distinguished from the true analyte of interest. In this manner, methyl amine may be distinguished from ethyl amine as the analyte being detected; methyl alcohol may be differentiated from ethyl alcohol; chloride ions may be discerned from bromide ions; and calcium ions may be discriminated from magnesium ions.

In many instances, however, this third and ultimate degree of precision and control will not be required for the purposes of the assay. Under these circumstances, it is necessary only that the substance employed as the metastable supersaturated developer solution be at least analogous to but not identical to, the condensation product formed by the reaction of the individual derivatizing agent and the particular analyte of interest. The desired degree of specificity, precision, and control therefore lies with the discretion of the user and the needs or circumstances of the individual application. There is no requirement or necessity that all three bases for selectivity and control be exercises. Rather, the availability of different levels of selectivity and control lies integrally within the method of the present invention; and the individual may exercise such degree of control as he finds necessary or appropriate.

It will be appreciated that the size and nature of the light scattering crystals formed and grown on the surface of the sensitized film as a result of the analyte's reaction with the selective developer solution are directly affected by the individual number of nucleating sites formed in-situ by the interaction of the analyte of interest with the individual derivatizing agent. In general, if the condensation reaction yields only a small quantity of reaction product, the number of individual nucleating sites are formed on the surface of the solid are relatively few. Alternatively, if the reaction of the individual derivatizing agent with the analyte of interest yields a relatively large quantity of reaction product, a proportionately larger number of individual nucleating sites will be formed on the surface of the solid substrate. The number of nucleating sites formed will control and determine the ultimate size of the crystals about to be grown since the amount of crystallizable material in the developer solution to be added subsequently will be divided equally among all the individual nucleating sites, each of which is identical in chemical composition to the other, regardless of their number. Accordingly, if a large number of individual nucleating sites are present on the surface, the quantity of crystallizing substance in the developer solution will be distributed over a greater number of nucleating sites; and consequently, the size of each crystal formed and grown will be relatively small. Conversely, if the number of individual nucleating sites formed are relatively few, the same concentration of crystallizable material in the developer solution will be equally distributed over a smaller number of individual nucleating sites, thereby causing a greater quantity of crystallizable material to be deposited on each site. This causes the formation of larger sized crystals. In all instances, however, the optically visible crystals forming the "developed image" are the result of adding the developer solution to the individual nucleating sites.

Quantitatively, therefore, the concentration of the crystallizable material comprising the metastable, supersaturated developer solution is important in that the concentration be of sufficient magnitude to provide for the growth of light scattering crystals which are optically detectable—even when that number of individual nucleating sites is at a maximum. For this reason, metastable supersaturated developer solutions are preferably prepared at a concentration ranging from 2-10 times saturation concentration. By using developer solutions of such concentration magnitude, rapid crystal formation and growth will occur after one or two minutes contact with the individual nucleating sites. In this manner, the speed of the assay methodology is maintained; maximum crystal growth is obtained within 5-10 minutes; and the growth of crystals is visibly complete in all respects in not more than 60 minutes time.

It will also be recognized that the control of the speed of matter deposition directly affects the ability of the grown crystals to be optically detected. For example, a rapid deposition of crystallizable material from the developer solution onto the individual nucleating sites tends to build up the crystal face toward an irregular point; whereas more leisurely deposition of crystallizable material produces a crystalline lattice whose crystal face is essentially flat. Optically, light is scattered more readily from crystals which have irregular and pointed faces and thus become more "visible" as a result of the light scattering effect. In comparison, flat-faced crystal lattices scatter light minimally and are more difficult to visualize with the unaided eye or with the use of specific crystal detection equipment. For this reason also, it is preferred that the concentration of the substances used in making metastable supersaturated developer solutions be as concentrated as possible in order to promote rapid deposition of the crystalline material when brought into reactive contact with the individual nucleating sites.

In view of the inherent instability of developer solutions when prepared in maximum concentration, it is most advisable to prepare the developer solution immediately prior to use. Furthermore, stabilizers such as polyvinyl alcohol, polyvinyl pyrrolidone, gelatin, agar, sodium carboxymethylcellulose, methyl and ethyl cellulose, and the like are useful and desirable for prolonging the effective life of the supersaturated developer solution in the present invention. As a practical matter therefore, it is convenient to have two prepared reagents available, one or both of which is in solution, which may be mixed together at a predetermined ratio on-site to form the prepared metastable supersaturated developer solution. The prepared developer solution may then be combined with the individual nucleating sites immobilized on the surface of the solid substrate to form the optically detectable crystals.

The result of forming and growing light scattering crystals in this manner gives rise to an optically observable and detectable change which can serve as both a qualitative and quantitative measure of the analyte of interest in a fluid test sample. The amount of optically detectable crystals formed provides a qualitative and/or quantitative measure which is correlatable with a calculated amount of an analyte of interest of a specific chemical class in the fluid sample. Typically, accurate quantitative results detecting the analyte of interest at concentrations less than the parts per million range may be reproducibly obtained within 10-15 minutes by the selective formation and growth of light scattering crystals in the manner described herein.

II. INDIVIDUAL DETAILS AND SCOPE OF THE PRESENT INVENTION

The assay methodology of the present invention is broadly and generally applicable to all presently known chemical classes of compositions both organic and inorganic in nature. The scope of the invention is without restriction or limitation to the composition, structure, orientation, or molecular format of any conventionally recognized chemical class—with one and only one exception: the chemical class comprising aldehydes and ketones, carbonyl containing compositions in general. In order to demonstrate the utility and applicability of the present assay methodology in this broad and general manner, on a diverse variety of chemical classes each having a singular identifying reactive entity representative of the individual class will be described and reviewed in detail seriatim. The diversity of specific chemical classes will include: organic and inorganic orders; aliphatic and aromatic families of organic compositions; and individual elemental atoms and molecules of inorganic substances; and individual specific chemical classes within each of these. By describing the individual details for each specific chemical class in this manner consistent with the more general detailed description provided previously herein, the attributes and applicability of the present invention will be more clearly and easily understood, recognized, and appreciated.

Chemical Class A: Nitrogeneous (Nitrogen Containing) Bases

This specific chemical class is characterized by an identifying reactive entity whose chemical composition and structure contains at least one nitrogen atom available for reaction with a proton or proton acceptor. The chemical class of nitrogeneous or nitrogen containing bases includes primary, secondary, and tertiary amines; hydrazines; and hydrazides. This chemical class therefore includes without exception all aliphatic, heterocyclic, and aromatic organic nitrogen containing compositions generally without regard to their complexity, size, or other properties. It is clearly understood also that this class explicitly includes ammonia, hydrazine, and hydroxylamine; those configurations and structures of nitrogen containing embodiments containing more than one nitrogen atom; and those embodiments in which a nitrogen atom is covalently bonded to a carbon atom by a plurality of bonds. The chemical structures classically terms hydroxylamines, imines, and semicarbazides are exemplary of such other embodiments specifically included within the membership of this chemical class.

Clearly, from the detailed description of the specific chemical class as a whole, the membership of this class is undeniably both large and extremely diverse. Nevertheless, each member of this large chemical class shares the common characteristic of having at least one nitrogen atom available for reaction with a proton or proton acceptor in a specified composition and organizational structural format. By this definition, each and every member of this class can be identified and distinguished from any other substance without confusion or ambiguity.

A listing of hazardous amines representative of this specific chemical class is provided by Table V below.

TABLE V

| DETECTABLE TOXIC AND HAZARDOUS AMINES | THRESHOLD LIMIT VALUES OF HUMAN TOXICITY* (parts/million) |
| --- | --- |
| 2-amino pyridine | 0.5 |
| aniline | 5 (skin) |
| butylamine | 5 |
| diethylamine | 25 |
| diethylamino ethanol | 10 (skin) |
| diisopropylamine | 10 |
| dimethylaniline | 5 |
| dimethylhydrazine | 0.5 |
| ethanolamine | 3 |
| ethylamine | 10 |
| ethylenediamine | 10 |
| ethyleneimine | 0.5 |
| N-ethyl morpholine | 20 (skin) |
| hydrazine | 1 (skin) |
| isopropylamine | 5 |
| methylamine | 10 |
| morpholine | 20 (skin) |
| phenyl hydrazine | 5 |
| propyleneinime | 2 (skin) |
| o-toluidine | 5 |
| triethylamine | 25 |
| xylidine | 5 (skin) |

*Threshold Limit Values And Biological Exposure Indices For 1987-88, 2nd printing, American Conference Of Governmental Industrial Hygienists, 1987.

The listing of Table V is illustrative of the membership of this nitrogeneous base chemical class and identifies specific pyridines, hydrazines, morpholines, imines, and other organic compositions—all of which contain at least one nitrogen atom as the identifying reactive entity. The listing of Table V is provided also as merely one listing representative of the many kinds of nitrogen containing bases which are desirably detected in small quantities because of their extremely toxic and hazardous effects on humans and animals. The threshold level of human toxicity for each member of this particular listing is in the parts per million range; and assays for their detection must be sufficiently sensitive, accurate, and specific to quantitatively detect these particular nitrogeneous bases at home, in the workplace, and in the ambient environment because of their harmful effects.

Due to the size and diversity of membership in this nitrogeneous base class generally, it is recognized that a number of different derivatizing agents may be usefully employed to prepare the sensitized films which are each selectively reactive with a nitrogen-containing analyte of interest to yield a reaction product formed in-situ as a plurality of immobilized, nucleating sites. The category of derivatizing agents selectively reactive for this chemical class includes the three types listed within Tables VI and VII respectively. In addition, the individual reaction product formed by each type of selective derivatizing agent within this category is represented by Reaction Schemes A below.

TABLE VI

| TYPE | AMINE DERIVATIZING AGENT TYPE NAME | PREFERRED EXAMPLES OF TYPE |
| --- | --- | --- |
| 1 | aryl aldehydes | p-dimethylamino benzaldehyde |
|  |  | p-dimethylaminocinnamaldehyde |
|  |  | o-,p-carboxy benzaldehyde |
|  |  | p-nitrobenzaldehyde |
|  |  | p-hydroxybenzaldehyde |
|  |  | terephthaldehyde |
|  |  | p-acetamido benzaldehyde |
|  |  | furfural |

TABLE VI-continued

| TYPE | AMINE DERIVATIZING AGENT TYPE NAME | PREFERRED EXAMPLES OF TYPE |
|---|---|---|
| | | 9-anthraldehyde |
| | | 4-biphenyl carboxaldehyde |
| | | 9-ethyl-3-carbazole carboxaldehyde |
| | | 2-fluorene carboxaldehyde |
| | | terephthaldicarboxaldehyde |
| | | 4-stilbene carboxaldehyde |
| | | 4-nitrocinnamaldehyde |
| 2 | aryl acids | 3,5-dinitrobenzoic acid |
| | | 5-nitro barbituric acid |
| | | picric acid |
| | | resorcyclic acid |
| | | p-toluene sulfonic acid |
| | | 2-nitrocinnamic acid |
| | | 3-nitrocinnamic acid |
| | | 4-nitrocinnaic acid |
| | | 4-benzoyl benzoic acid |
| | | 2,3-napthalene carboxylic acid |
| | | 2,6-napthalene carboxylic acid |
| | | terephthalic acid |
| 3 | sodium tetraphenyl boron | sodium tetraphenylboron |

TABLE VII

| AMINE TO BE DETECTED | PREFERRED DERIVATIZING AGENT TYPE | EXAMPLE | PREFERRED DEVELOPER SOLUTION |
|---|---|---|---|
| 2-aminopyridene | 1 | 4-carboxybenzaldehyde | 4-carboxy benzaldehyde-2-iminopyridine |
| aniline | 1 | 4-carboxybenzaldehyde | anilino-4-carboxybenzaldehyde |
| butylamine | 3 | sodium tetraphenyl boron | butylamine TPB* |
| diethylamine | 3 | sodium tetraphenyl boron | diethyamine TPB* |
| diethylamino ethanol | D | 3,5-dinitrobenzoic acid | diethylamino ethanol 3-5 dinitrobenzoate |
| diisopropyl amine | 2 | 5-nitrobarbituric acid | diisopropylamine 5-nitrobarbiturate |
| dimethylamine | 3 | sodium tetraphenyl boron | dimethylamine TPB* |
| dimethylaniline | 3 | sodium tetraphenyl boron | dimethylaniline TPB* |
| dimethylhydrazine | 3 | sodium tetraphenyl boron | dimethyl hydrazine TPB* |
| ethanolamine | 2 | 5-nitro barbituric acid | ethanolamine 5-nitrobarbiturate |
| ethylenediamine | 3 | sodium tetraphenyl boron | ethylenediamine TPB* |
| ethyleneimine | 3 | sodium tetraphenyl boron | ethyleneimine TPB* |
| N-ethyl morpholine | 2 | 3,5-dinitrobenzoic acid | N-ethylmorpholine-3-5 nitrobenzoate |
| hydrazine | 1 | 4-carboxybenzaldehyde | 4-carboxybenzaldehyde hydrazone |
| isopropylamine | 3 | sodium tetraphenyl boron | isopropylamine TPB* |
| methylamine | 3 | sodium tetraphenyl boron | methylamine TPB* |
| morpholine | 3 | sodium tetraphenyl boron | morpholine TPB* |
| phenylhydrazine | 1 | 4-carboxybenzaldehyde | 4-carboxybenzaldehyde phenylhydrazone |
| propyleneimine | 3 | sodium tetraphenyl boron | propyleneimine TPB* |
| o-toluidine | 1 | 4-carboxybenzaldehyde | o-toluidino-4-carboxy benzaldehyde |
| triethylamine | 3 | sodium tetraphenyl boron | triethylamine TPB* |
| xylidine | 1 | 4-carboxybenzaldehyde | xylidino-4-carboxy benzaldehyde |
| nicotine | 3 | sodium tetraphenyl boron | nicotine TPB* |

TABLE VII-continued

| AMINE TO BE DETECTED | PREFERRED DERIVATIZING AGENT TYPE EXAMPLE | PREFERRED DEVELOPER SOLUTION |
|---|---|---|
| | boron | |

*TPB = tetraphenyl borate

Reaction Scheme A

ArCHO + RNH$_2$ $\longrightarrow$ ArCH=NR$_2$     (A1)
aryl aldehyde   primary amine   Schiff's base

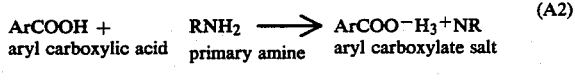

ArCOOH + RNH$_2$ $\longrightarrow$ ArCOO$^-$H$_3$$^+$NR   (A2)
aryl carboxylic acid   primary amine   aryl carboxylate salt

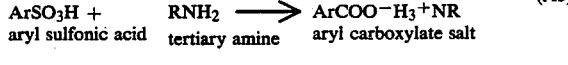

ArSO$_3$H + RNH$_2$ $\longrightarrow$ ArCOO$^-$H$_3$$^+$NR   (A3)
aryl sulfonic acid   tertiary amine   aryl carboxylate salt C$_{24}$H$_{20}$BNa + R$_2$NH $\longrightarrow$ C$_{24}$H$_{20}$B$^-$H$_2$$^+$NR$_2$   (A4)
sodium tetraphenyl boron   secondary amine   tetraphenyl borate salt

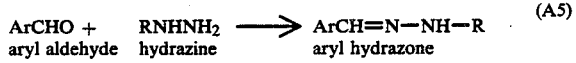

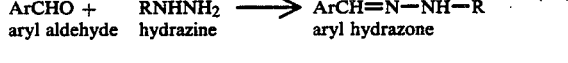

ArCHO + RNHNH$_2$ $\longrightarrow$ ArCH=N—NH—R   (A5)
aryl aldehyde   hydrazine   aryl hydrazone

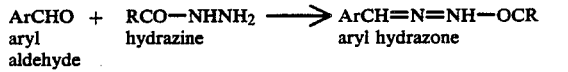

ArCHO + RCO—NHNH$_2$ $\longrightarrow$ ArCH=N=NH—OCR   (A6)
aryl aldehyde   hydrazine   aryl hydrazone Table VI identifies three types of derivatizing agents: aryl aldehydes; aryl acids; and sodium tetraphenyl boron. Preferred examples of each type are also specifically provided—the nature, attributes, and preparation of which are all conventionally known in this art. Table VII identifies the preferred derivatizing agents by type and illustrative example for each nitrogeneous base analyte previously listed within Table V. Similarly, Reaction Scheme A identifies the result of combining each type of derivatizing agent and representative members of this specific class—in terms of their reaction with the sensitized film for nitrogeneous bases and the reaction product formed in-situ as a plurality of immobilized, nucleating sites. It is clear via Reactions A1–A6 respectively that the yielded reaction products are of different formulations and structures; and that each reaction product is unique.

After the reaction of the derivatizing agent with an analyte of interest chosen from this specific chemical class, the reaction product (or latent image) which is present as immobilized, nucleating sites then treated with a metastable supersaturated developer solution which causes the formation of a plurality of optically detectable light scattering crystals. In conformity with the general principles of the present assay methodology, it is preferred, although not absolutely required, that the substance comprising the metastable supersaturated developer solution be identical to the reaction product yielded by the selective derivatizing agent and the nitrogen containing analyte of interest. Accordingly, Table VII provides a listing of the preferred developer solutions for each nitrogen containing analyte to be detected—a listing which is in fact identical to the individual reaction product of the specific analyte identified and the preferred derivatizing agent provided. In this way, a maximum degree of assay selectivity and accuracy is provided. Alternatively, however, the substance comprising the metastable supersaturated developer solution may be an analogue of that substance preferred within Table VII. Under these circumstances, the phenomenon known as "epitaxy" is therefore employed to obtain the formation of light scattering crystals. Table VII, however, provides for complete chemical identity between the material of the nucleating sites and the composition of the metastable supersaturated developer solution as the best mode of practicing the present invention.

Accordingly, following the general description and principles of the assay methodology previously described, the combination of the preferred developer solution with the formed reaction product of the selective derivatizing agent and the nitrogenous base analyte (present as a plurality of immobilized, nucleating sites) will yield optically detectable crystals in both quantitative and qualitative degree. All that the user need then do, therefore, is to detect the presence of the formed light scattering crystals as a measure of the specific analyte of interest in the original sample. This detection may be achieved by the unaided eye or by any other means including instrumentation if this is considered desirable or useful under the circumstances.

Chemical Class B: Alcohols

The chemical class of alcohols comprises a large and diverse membership wherein each member comprises at least one hydroxyl group as the identifying reactive entity. The hydroxy group composition and structure (—OH) identifies every member of this class. The only other requirement for membership within this specific chemical class is the presence of at least an organic moiety as the organic component bearing at least one hydroxyl group which is available for reaction; however, the optional presence of other structures or entities in addition to the organic moiety is explicitly intended. There is no upper limit, however, on the number of individual hydroxyl groups which may in fact be present within the analyte; nor is there any limitation whatsoever on the formulation or organizational structure of the organic moiety so long as the requisite hydroxyl group itself is present. Accordingly, the membership of this specific chemical class includes primary alcohols, secondary alcohols, tertiary alcohols, diols and polyols, glycols, glycerols, cyclic diols and cyclic polyols. The detection of the specific chemical class comprising alcohols is illustrated by Tables VIII and IX respectively, and Reaction Scheme B below.

TABLE VIII

| TYPE | ALCOHOL DERIVATIZING AGENT TYPE NAME | PREFERRED EXAMPLE OF TYPE |
|---|---|---|
| 1 | aryl isocyanates | α-naphthyl isocyanate |
|   |   | phenyl isocyanate |
|   |   | p-anisyl isocyanate |
|   |   | p-chlorophenyl isocyanate |
|   |   | 3,5-dinitrophenyl isocyanate |
|   |   | p-iodophenyl isocyanate |
|   |   | o-, m-, and p-nitrophenyl isocyanate |
| 2 | aryl nitro acid halides | p-nitrobenzoyl chloride |
|   |   | 3,5-dinitrobenzoyl chloride |
|   |   | 3,4,5-triiodobenzoyl chloride |
| 3 | pseudosaccharin chloride | pseudosaccharin chloride |

TABLE IX

| ALCOHOL TO BE DETECTED | PREFERRED DERIVATIZING AGENT TYPE | EXAMPLE | PREFERRED DEVELOPER SOLUTION |
|---|---|---|---|
| methyl alcohol | 1 | α-napthyl isocyanate | methyl-α-napthyl urethane |
| n-propyl alcohol | 1 | α-napthyl isocyanate | n-propyl-α-napthyl urethane |
| cyclopentanol | 1 | α-napthyl isocyanate | cyclopentyl-α-napthyl urethane |
| 2-methylcyclohexanol | 1 | α-napthyl isocyanate | 2-methylcyclohexyl α-napthyl urethane |
| 4-methylcyclohexanol | 1 | α-napthyl isocyanate | 4-methylcyclohexyl α-napthyl urethane |
| isopropyl alcohol | 2 | 3,5-dinitrobenzoyl chloride | isopropyl-3,5-dinitrobenzoate |
| tert-amyl alcohol | 2 | 3,5-dinitrobenzoyl chloride | tert-amyl-3,5-dinitrobenzoate |
| 2-pentanol | 2 | 3,5-dinitrobenzoyl chloride | 2-pentyl-3,5-dinitrobenzoate |
| cyclohexanol | 2 | 3,5-dinitrobenzoyl chloride | cYclohexyl-3,5-dinitrobenzoate |
| ethylene glycol | 2 | 3,5-dinitrobenzoyl chloride | ethylene glycol-3,5-dinitrobenzoate |
| n-heptyl alcohol | 3 | pseudosaccharin chloride | pseudosaccharin n-heptyl ether |
| benzyl alcohol | 3 | pseudosaccharin chloride | pseudosaccharin benzyl ether |
| n-nonyl alcohol | 3 | pseudosaccharin chloride | pseudosaccharin n-nonyl ether |
| cinnamyl alcohol | 3 | pseudosaccharin chloride | pseudosaccharin cinnamyl ether |

Reaction Scheme B

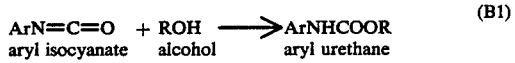
$$ArN=C=O + ROH \longrightarrow ArNHCOOR \quad (B1)$$
aryl isocyanate    alcohol    aryl urethane

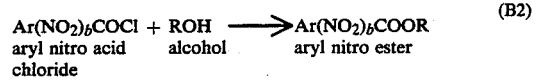
$$Ar(NO_2)_bCOCl + ROH \longrightarrow Ar(NO_2)_bCOOR \quad (B2)$$
aryl nitro acid chloride    alcohol    aryl nitro ester

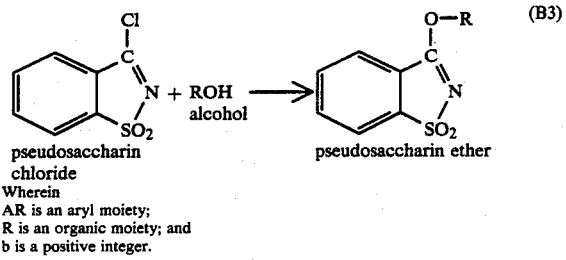
(B3)

pseudosaccharin chloride          pseudosaccharin ether

Wherein
AR is an aryl moiety;
R is an organic moiety; and
b is a positive integer.

The chemical class of alcohols as a whole is merely represented by the individual analytes listed within Table IX, each of which is correlated with a preferred type and example of a selective derivatizing agent; and with a preferred developer solution able to yield light scattering crystals. The analytes listed within Table IX are illustrative of the class membership generally, each of which has at least one hydroxyl moiety as the identifying reactive entity indicative of the class. The derivatizing agents are categorized by type and provide examples of some of the agents able to selectively react with a hydroxyl containing analyte of interest to yield a reaction product formed in-situ as a plurality of immobilized, nucleating sites. The types of derivatizing agent useful for preparing a sensitized film are listed within Table VIII as aryl isocyanates; aryl nitroacid halides; and pseudosaccharin chloride. Individual preferred examples of each type of selective derivatizing agent are also provided by Table VIII.

The reaction products formed by each type of derivatizing agent are illustrated within Reaction Scheme B and by Reactions B1, B2, and B3 respectively. Each reaction product made in accordance with these reaction schemes is intended to be formed in-situ upon the exposed sensitized film for alcohols as a plurality of immobilized, nucleating sites. After the formation of these nucleating sites is achieved, the addition of a metastable supersaturated developer solution will cause the submicroscopic latent image to grow into optically visible crystals. The preferred developer solutions for each analyte represented are identified Within Table IX. Also noted previously, the preferred developer solution is identical in composition to the reaction product of the hydroxyl bearing analyte of interest with the selective derivatizing agent; and will cause the formation of light scattering crystals as a measure of the analyte of interest in the test sample. Again, as previously stated, the preferred developer solution is identical to the reaction product present within the nucleating sites immobilized on a solid substrate. Alternatively, a developer solution which is merely an analogue of the material comprising the nucleating sites can also be usefully employed for the formation and growth of light scattering crystals, recognizing that the selectivity and control of the assay is somewhat diminished by use of the analogue composition.

Chemical Class C: phenols

The chemical class of phenols comprises a large and diverse membership wherein the organic moiety comprises an aryl composition and each member within this class comprises at least one hydroxyl group as the identifying reactive entity. This chemical formulation and organizational structure identifies each member of this class and distinguishes it from every other organic composition. There is no upper limit, however, on the number of individual hydroxyl groups which may in fact be present within the aryl analyte; nor is there any limitation whatsoever on the composition or structure of the aromatic organic moieties bearing at least one hydroxyl group. Accordingly, the membership of this specific chemical class includes phenols, hydroquinones, naphthols, and anthrahydroquinones. The detection of the chemical class comprising phenols is illustrated by Tables X and XI respectively, and Reaction Scheme C as follows.

TABLE X

| TYPE | PHENOL DERIVATIZING AGENT TYPE NAME | PREFERRED EXAMPLE OF TYPE |
|---|---|---|
| 1 | aryl isocyanates | α-naphthyl isocyanate<br>phenyl isocyanate<br>p-anisyl isocyanate<br>p-chlorophenyl isocyanate<br>3,5-dinitrophenyl isocyanate<br>p-iodophenyl isocyanate<br>o-, m-, and p-nitrophenyl isocyanate |
| 2 | 2,4-dinitrochlorobenzene | 2,4-dinitrochlorobenzene |
| 3 | pseudosaccharin chloride | pseudosaccharin chloride |

TABLE XI

| PHENOL TO BE DETECTED | PREFERRED DERIVATIZING AGENT | |
|---|---|---|
| | TYPE | EXAMPLE | |
| o-chlorophenol | 1 | α-naphthyl isocyanate | o-chlorophenyl-α-napthyl urethane |
| o-bromophenol | 1 | α-naphthyl isocyanate | o-bromophenyl-α-napthyl urethane |
| thymol | 1 | α-naphthyl isocyanate | thymol napthyl urethane |
| mesitol | 1 | α-naphthyl isocyanate | mesitol napthyl urethane |
| m-nitrophenol | 1 | α-naphthyl isocyanate | m-nitrophenol napthyl urethane |
| eugenol | 2 | 2,4-dinitrochlorobenzene | 2,4-dinitrophenyl euginol ether |
| isoeugenol | 2 | 2,4-dinitrochlorobenzene | 2,4-dinitrophenyl isoeugenol ether |
| o-nitrophenol | 2 | 2,4-dinitrochlorobenzene | 2,4-dinitrophenyl o-nitrophenyl ether |
| vanillin | 2 | 2,4-dinitrochlorobenzene | 2,4-dinitrophenyl vanillin ether |
| resorcinol | 2 | 2,4-dinitrochlorobenzene | 2,4-dinitrophenyl resorcinol ether |
| hydroquinone | 2 | 2,4-dinitrochlorobenzene | 2,4-dinitrophenyl bis hydroquinone ether |
| phenol | 3 | pseudosaccharin chloride | pseudosaccharin phenyl ether |
| p-cresol | 3 | pseudosaccharin chloride | pseudosaccharin p-cresol ether |
| p-methoxyphenol | 3 | pseudosaccharin chloride | pseudosaccharin p-methoxyphenyl ether |
| 2,4,6-trimethylphenol | 3 | pseudosaccharin chloride | pseudosaccharin 2,4,6-trimethyl phenyl ether |
| 2-naphthol | 3 | pseudosaccharin chloride | pseudosaccharin 2-naphthyl ether |

Reaction Scheme C

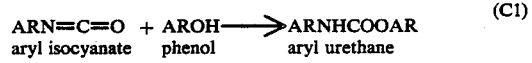

(C1)

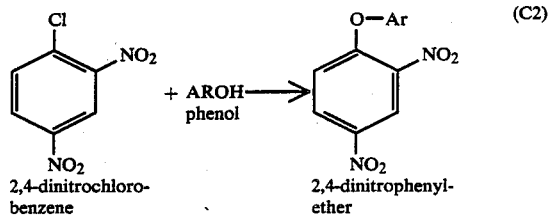

(C2)

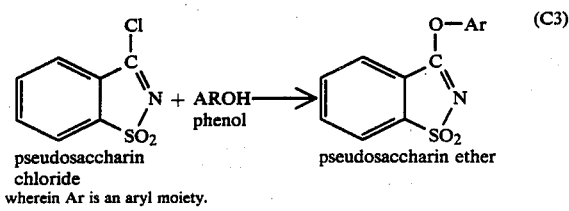

(C3)

wherein Ar is an aryl moiety.

The specific class of phenols as a whole is represented by the analytes listed within Table XI, each of which is correlated with a preferred type and example of selective derivatizing agent; and with a preferred developer solution able to yield light scattering crystals. The analytes listed within Table XI are exemplary of the membership generally within this specific class, each of which is an aryl composition and has at least one hydroxyl moiety as the identifying reactive entity indicative of the specific class. The derivatizing agents are categorized by type and provide a variety of agents able to selectively react with an analyte of interest from this specific chemical class to yield a reaction product formed in-situ upon the exposed sensitized film for phenols as a plurality of immobilized, nucleating sites. The types of derivatizing agent are listed within Table X as aryl isocyanates; 2,4-dinitrobenzene; and pseudosaccharin chloride. Some preferred examples of these selective derivatizing agents are also provided by Table X.

The reaction products yielded by each type of derivatizing agent and the membership of this specific chemical class are illustrated within Reaction Scheme C and by Reactions C1, C2, and C3 respectively. Each reaction product yielded in accordance with these reaction schemes is to be formed in-situ as a plurality of immobilized, nucleating sites on the exposed sensitized film for phenols. Subsequently, the addition of a prepared metastable supersaturated developer solution will result in the formation of visible crystals. The preferred developer solutions for each analyte represented are identified within Table XI individually. Also, as noted previously, the preferred developer solution is one identical in composition to the reaction product of the analyte of interest with the selective derivatizing agent. Alternatively, a developer solution which is merely an analogue of the material comprising the nucleating sites can also be usefully employed for the formation and growth of light scattering crystals, recognizing that the selectivity and control of the assay is somewhat diminished by use of the analogue.

Chemical Class D: Alkyl Halides

The specific chemical class of organic alkyl halides includes all aliphatic analytes having at least one halide atom as a chemical constituent. The halides class conventionally includes flouride, chloride, bromide, and iodide—each of which may serve as the identifying

TABLE XII

| TYPE | ALKYL HALIDE DERIVATIZING AGENT TYPE NAME | PREFERRED EXAMPLE OF TYPE |
|---|---|---|
| 1 | thiophenols | 2,4-dinitrothiophenol |
| 2 | mercapto-thioazoles | 6-nitro,2-mercapto-benzothioazole |

TABLE XIII

| ALKYL HALIDE TO BE DETECTED | PREFERRED DERIVATIZING AGENT | PREFERRED DEVELOPER SOLUTION |
|---|---|---|
| methyl chloride | 2,4-dinitrothiophenol | 2,4-dinitrophenyl methyl sulfide |
| tertiary butyl chloride | 2,4-dinitrothiopbenol | 2,4-dinitrophenyl tertiary butyl sulfide |
| benzyl chloride | 2,4-dinitrothiophenol | 2,4-dinitrophenyl benzyl sulfide |
| isobutyl bromide | 2,4-dinitrohiophenol | 2,4-dinitrophenyl isobutyl sulfide |
| cetyl bromide | 2,4-dinitrothiophenol | 2,4-dinitrophenyl cetyl sulfide |
| isoamyl iodide | 2,4-dinitrothiophenol | 2,4-dinitrophenyl isoamyl sulfide |
| n-amyl iodide | 2,4-dinitrothiophenol | 2,4-dinitrophenyl n-amyl sulfide |
| cyclohexyl bromide | 6-nitro-2-mercapto benzothiazole | cyclohexyl-6-nitro-benzothiazolyl sulfide |
| ethyl bromide | 6-nitro-2-mercapto benzothiazole | ethyl-6-nitro-benzothiazolyl sulfide |
| n-heptyl chloride | 6-nitro-2-mercapto benzothiazole | n-heptyl-6-nitro-benzothiazolyl sulfide |
| n-hexyl bromide | 6-nitro-2-mercapto benzothiazole | n-hexyl-6-nitro-benzothiazolyl sulfide |
| 1,1-diiodomethane | 6-nitro-2-mercapto benzothiazole | 2,2'(methylene dithio) bis (6-nitro) benzothiazole |
| 1,4-dichlorobutane | 6-nitro-2-mercapto benzothiazole | 2,2'(butylene dithio) bis (6-nitro) benzothiazole |

Reaction Scheme D

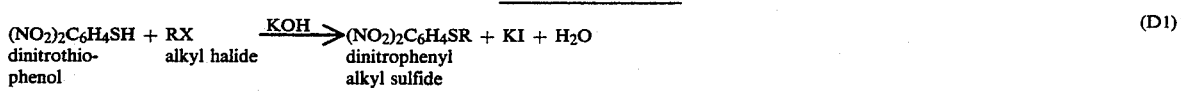
(D1)

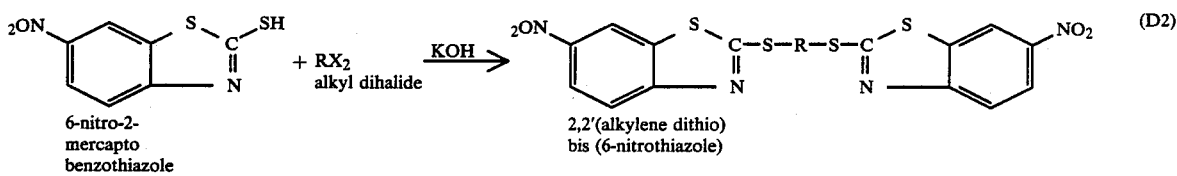
(D2)

reactive entity whose presence identifies an analyte of interest as being within this specific chemical class. In addition, this chemical class is sufficiently broad in its membership to include alkyl halides, cycloalkyl halides, and alkyl dihalides of various formulations and organizational structures. The halide constituent of the analyate may be present as a single atom or as a plurality of atoms located at different positions within the molecular alkyl structure. It is also intended that there is no meaningful restriction or limitation as to the composition or structure of the alkyl organic moiety bearing the halide itself.

The assay methodology of the present invention employed for the detection of members within the chemical class of alkyl halides is detailed by Tables XII and XIII and Reaction Schemes D below.

A representative, but non-exhaustive listing of organic halides able to be detected by the present assay methodology is provided by Table XIII. It is clear that the membership of this specific chemical class varies substantially in formulation, structure, and chemical reactivity. For this reason, two types of selective derivatizing agents are provided by Table XII and preferably employed as sensitized films for detecting alkyl halides: thiophenols and mercapto-thioazoles. Preferred examples of using each derivatizing agent are shown by Table XIII.

When the preferred derivatizing agent is combined with the alkyl halide analyte of interest, a reaction comparable to those provided by Reaction Schemes D is provided Reaction D1 indicates a reaction product which is a dinitrophenyl alkyl sulfide; Reaction D2 provides an alkalene bis-nitrobenzothiazole as the product. In each instance, the reaction product is formed in-situ as a plurality of immobilized, nucleating sites, upon the exposed sensitized film for alkyl halides serving as a solid substrate. It will be appreciated also that both derivatizing agents are selectively reactive with the halide components of the organic analyte; and in each instance provides a reaction product which is chemically unique and distinguishable from the reaction product yielded by the other members of this class which are similar or analogous to the individual analyte of interest.

After the reaction product has been formed as immobilized, nucleating sites, they are treated with a metastable supersaturated solution which is preferrably identical to the reaction product yielded by the selective derivatizing agent and the analyte of interest. A listing of the preferred developer solutions for the individual analyte to be detected is provided by Table XIII. It is again emphasized that the preferred developer solution substance is itself identical to the reaction product of the derivatizing agent and the analyte of interest, but this is not an absolute requirement. Clearly, a substance which is at least an analogue or homologue of the true reaction product will also be effective to cause the formation of optically detectable light scattering crystals. Combining the preferred developer solution (or its analogous counterpart) with the immobilized, nucleating sites provides optically visible crystals which are a measure of the alkyl halide analyte in the test sample. It is also understood that the nature, size, and form of the light scattering crystals themselves will conform to the conditions and descriptions previously detailed herein.

Chemical Class E: Organic Acids

The chemical class of organic acids is one of extreme size and disparity. Such organic acids include both carboxylic acid and sulfonic acid forms—each of which contains alkyl and aryl members. Accordingly, therefore, the identifying reactive entity for this specific chemical class take either of two forms: as a carboxylic group (R—COOH); and as a sulfonic group (R—$SO_3H$)— the chemical composition and structure of which identifies each member within this class from other chemical compositions. A feature of the members within this class is that each organic acid is a proton donor and, under proper conditions, are able to donate a proton during chemical reaction. In addition, while it is required that at least one carboxyl or sulfonyl moiety be present as a constituent part of the analyte of interest, there is no limit as to the actual number of carboxylic groups or sulfonic groups (the identifying reactive entity) actually present within the molecular structure of the analyte. Clearly, therefore, dicarboxylic and tricarboxylic organic acids are members of this specific chemical class. Similarly, organic analytes having a plurality of sulfonic acid groups as constituent parts of the molecular structure are also members of this chemical class.

The reagents used to prepare a sensitized film for the detection of carboxylic acids and sulfonic acids are described by Tables XIV and XV, and Reaction Scheme E below.

TABLE XIV

| ORGANIC ACID TYPE | DERIVATIZING AGENT TYPE NAME | PREFERRED EXAMPLE OF TYPE |
|---|---|---|
| 1 | aryl amines | benzyl amine |

TABLE XIV-continued

| ORGANIC ACID TYPE | DERIVATIZING AGENT TYPE NAME | PREFERRED EXAMPLE OF TYPE |
|---|---|---|
| | | p-nitrobenzylpyridine |
| | | piperazine |
| | | m-nitroaniline |
| | | benzidine |
| | | p-phenylenediamine |
| | | aminoacetophenone |
| | | p-toluidine |
| 2 | substituted thioureas | s-benzylisothiouronium chloride |
| | | s-p-broomobenzylthiouronium chloride |
| | | s-p-chlorobenzylthiouronium chloride |
| | | s-l-napthylmethylthiouronium chloride |
| | | s-p-nitrobenzylisothiouronium chloride |

TABLE XV

| ORGANIC ACID TO BE DETECTED | PREFERRED DERIVATIZING AGENT | PREFERRED DEVELOPER SOLUTION |
|---|---|---|
| acetic | p-toluidine | p-toluidinium acetate |
| propionic | p-toluidine | p-toluidinium propidate |
| dichloroacetic | p-toluidine | p-toluidinium dichloroacetate |
| stearic | p-toluidine | p-toluidinium stearate |
| benzoic | p-toluidine | p-toluidinium benzoate |
| nitrobenzoic | piperazine | piperazinium nitrobenzoate |
| phthalic | piperazine | piperazinium phthalate |
| methoxybenzoic | piperazine | piperazinium methoxybenzoate |
| oxalic | piperazine | piperazinium oxalate |
| cinnamic acid | piperazine | piperazinium cinnamate |
| benzenesulfonic acid | 5-benzylisothiouronium chloride | s-benzylisotbiouronium benzene sulfonate |
| p-toluenesulfonic acid | 5-benzylisothiouronium chloride | s-benzylisothiouronium toluene sulfonate |
| m-nitrobenzene sulfonic acid | 5-benzylisothiouronium chloride | s-benzylisothiouronium nitrobenzene sulfonate |
| ethane sulfonic acid | 5-benzylisothiouronium chloride | s-benzylisothiouronium ethane sulfonate |
| 1-napthylamine sulfonic acid | 5-benzylisothiouronium chloride | s-benzylisothiouronium 1-napthylamine sulfonate |

Reaction Scheme E

sulfonic acid    aryl amine    aryl amine sulfonate    (E1)

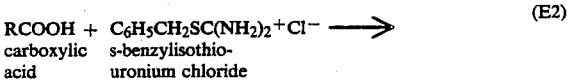
carboxylic acid    s-benzylisothiouronium chloride    (E2)

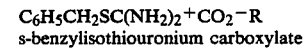
s-benzylisothiouronium carboxylate

Wherein Ar is an aryl moiety; and R is an organic moiety.

Table XV provides a representative listing of organic acids able to be detected by the present assay methodology. The analytes include saturated and unsaturated molecules; alkyl and aryl moieties; and substituted and unsubstituted acids.

In view of the immense membership and chemical variety of this chemical class, two types of selective derivatizing agents are preferred as indicated by Table XIV. These are: aryl amines and substituted thioureas, preferred examples of each type being listed. When either type of selective derivatizing agent is combined with an organic acid, the reactions shown by Reaction Scheme E occur. Reaction E1 identifies the reaction between an aryl amine and a sulfonic acid analyte of interest; alternatively, Reaction E2 describes the reaction between a carboxylic acid and a substituted thiourea. Reactions E1 and E2 are representations of the general reactions occurring between each type of selective derivatizing agent and an analyte of interest which is a member of this chemical class. In each instance also, the reaction product is yielded as a plurality of immobilized, nucleating sites on the surface of the exposed sensitized film for organic acids.

After the reaction products exemplified by Reaction Scheme E are formed in-situ as a plurality of immobilized, nucleating sites on the solid substrate, this product is treated with a metastable supersaturated developer solution such that a plurality of optically detectable, light scattering crystals are formed. The preferred substances used for the developer solution are indicated by Table XV for the representative listing of carboxylic acid analytes. The preferred developer solution substance again is identical with the individual reaction product formed by the particular analyte and the selective derivatizing agent in order that maximum selectivity and accuracy of detection be obtained. Alternatively, it is required only that the substance comprising the developer solution be at least an analogue of the reaction product yielded by the selective derivatizing agent and the individual analyte in accordance with the general principles of the present assay methodology. The combination of the developer solution with the immobilized, nucleating sites provides a plurality of optically detectable crystals which serve as a measure of the carboxylic acid analyte of interest in a test sample.

Chemical Class F: Thiols And Mercaptans

The chemical class of thiols and mercaptans is a separate and distinct chemical class due to the nature of the identifying reactive entity indicative of the chemical class, a sulfur containing moiety (—SH). It is the presence of at least one sulfur atom within the composition which identifies the particular analyte both in chemical composition and structure as being within this specific chemical class. The membership is conventionally divided into aliphatic thiols traditionally termed "mercaptans"; and aryl thiols traditionally termed "thiophenols." Clearly, the presence of the sulfhydrl group serves as the identifying reactive entity which identifies all members within this specific chemical class and distinguishes them from all other compositions generally.

The assay reagents for detecting thiols and mercaptans are described by Tables XVI and XVII, and by Reaction Scheme F respectively.

TABLE XVI

| TYPE | THIOL OR MERCAPTAN DERIVATIZING AGENT TYPE NAME | PREFERRED EXAMPLES OF TYPE |
|---|---|---|
| 1 | halide substituted nitrobenzenes | 2,4-dinitrochlorobenzene |
| 2 | transition metal salts | lead nitrate cupric chloride |

TABLE XVII

| THIOL OR MERCAPTAN TO BE DETECTED | PREFERRED DERIVATIZING AGENT | PREFERRED DEVELOPER SOLUTION |
|---|---|---|
| methyl mercaptan | 2,4-dinitrochlorobenzene | 2,4-dinitrophenyl methyl sulfide |
| ethyl mercaptan | 2,4-dinitrochlorobenzene | 2,4-dinitrophenyl ethyl sulfide |
| n-butyl mercaptan | 2,4-dinitrochlorobenzene | 2,4-dinitrophenyl n-butyl sulfide |
| cyclohexyl mercaptan | 2,4-dinitrochlorobenzene | 2,4-dinitrophenyl cyclohexyl sulfide |
| benzyl mercaptan | 2,4-dinitrochlorobenzene | 2,4-dinitrophenyl benzyl sulfide |
| amyl mercaptan | 2,4-dinitrochlorobenzene | 2,4-dinitrophenyl amyl sulfide |
| thiophenol | 2,4-dinitrochlorobenzene | 2,4-dinitrophenyl phenol thio ether |
| o, thiocresol | lead nitrate | lead dicresol-mercaptide |
| p, thiocresol | lead nitrate | lead di-p-cresol mercaptide |
| p-chlorothiophenol | lead nitrate | lead d-p-chlorophenyl mercaptide |

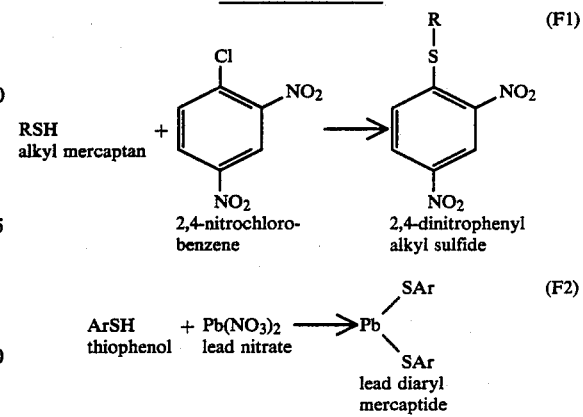

Reaction Scheme F

R = alkyl moiety
Ar = aryl moiety

Table XVII identifies a representative listing of thiophenols and mercaptans which can be detected using the assay methodology of the present invention. For this purpose, two types of selective derivatizing agents are provided: halide substituted nitrobenzenes and transition metal salts. Preferred examples of each type of selective derivatizinq agent able to selectively react with an analyte of interest which is either a mercaptan or a thiophenol are provided by Table XVI. The nature of reaction and the resulting reaction products are described by Reaction Scheme F. Reaction F1 describes the reaction between an alkyl mercaptan analyte and a halide substituted nitrobenzene. Similarly, Reaction F2 identifies the product of combining a transition metal salt (lead nitrate) with a thiophenol analyte of interest. In each instance, the individual reaction product is formed in-situ as a plurality of immobilized, nucleating sites on the surface of the exposed sensitized film for thiols and mercaptans. It will be recognized also that in each instance, the individual analyte of interest combines with the selective derivatizing agent to yield a unique, chemically distinct reaction product formed as the nucleating sites.

Subsequent to the formation of the immobilized nucleating sites, the reaction product material formed in-situ on the solid substrate is treated with a metastable supersaturated developer solution preferably comprising a substance which is identical to the reaction product of the selective derivatizing agent and the individual thiol or mercaptan analyte of interest. For the analytes representing the specific chemical class as a whole, a preferred listing of developer solutions is provided by the data of Table XVII. Alternatively, however, a developer solution comprising a substance which is an analogue or a homologue of the individual reaction product yielded by the selective derivatizing agent and the analyte may be employed, the degree of similarity varying with the nature of the reaction product and the analyte itself. In each instance, it is required only that the result of treating the immobilized, nucleating sites with the developer solution yield a plurality of optically detectable, light scattering crystals. By optically detecting the presence of these light-scattering crystals, a qualitative and/or quantitative measure of the individual analyte of interest can be made in an accurate and reproducible manner.

Chemical Class G: Hydrocarbons (Aromatic And Aliphatic)

This specific chemical class comprises one of the larger chemical classes in terms of membership, but offers less diversity of chemical structure and composition than many other classes. The membership of this chemical class is identifiable by the specific composition and structure of the individual analyte as a whole molecule, the individuality of the formula constituents and overall structure serving as the identifying reactive entity which marks the analyte as being of this specific chemical class. The identifying reactive entity is therefore unique and distinguishable from other specific chemical classes which utilize only a moiety or a component part of the analyte as the means for identification. An alternate format exists and is required for this chemical class which comprises aromatic and aliphatic hydrocarbons. In each instance, it is the entirety of the molecule as a whole including its chemical composition and structure which alone identifies the analyte as being within this specific class.

By definition, this class includes not only simple aromatic and aliphatic hydrocarbons but also substituted hydrocarbons within its membership. The controlling terminology is "hydrocarbon" which demands that the analyte be composed of carbon and hydrogen. In addition, it is required that the molecule to be detected be either an aromatic hydrocarbon—that is, be composed of benzene and compounds that resemble benzene in chemical behavior; or an aliphatic hydrocarbon—that is a molecule composed of alkyl or parraffin hydrocarbon units. Included in this class also are aromatic hydrocarbons which are aryl halides—this is, aromatic hydrocarbons containing a ring substituted halogen atom (flourine, chlorine, bromine, or iodine). There is, however, no requirement whatsoever regarding the degree of saturation or unsaturation for any member within this class. Accordingly, the analyte of interest may be either completely saturated, completely unsaturated, or contain both saturated and unsaturated components within its overall structure.

The assay methodology for detection of aromatic and aliphatic hydrocarbons is described by the data of Tables XVIII and XIX, and Reaction Scheme G respectively.

TABLE XVIII

| TYPE | HYDROCARBON DERIVATIZING AGENT TYPE NAME | PREFERRED EXAMPLES OF TYPE |
|---|---|---|
| | FOR AROMATICS | |
| 1 | nitrophenols and nitroquinones | picric acid 2,4,7-trinitrofluorenone |
| | FOR ALIPHATICS | |
| 2 | ureas | α-dinitrophenanthrene quinone chrysaminic acid α-dinitroanthraquinone urea thiourea |

TABLE XIX

| AROMATIC AND ARENE HYDROCARBONS TO BE DETECTED | PREFERRED DERIVATIZING AGENT | PREFERRED DEVELOPER SOLUTION |
|---|---|---|
| 1,2-dimethyl benzene | 2,4,7-trinitro fluorenone | 2,4,7-trinitro fluorenone 1,1,2-dimethyl benzene addition compound |
| 1,3-dimethyl benzene | 2,4,7-trinitro fluorenone | 2,4,7-trinitro fluorenone 1,3-dimethyl benzene addition compound |
| 1,2,4,5-tetramethyl benzene | 2,4,7-trinitro fluorenone | 2,4,7-trinitro fluorenone 1,2,4,5-tetramethyl benzene addition compound |
| bromobenzene | 2,4,7-trinitro fluorenone | 2,4,7-trinitro fluorenone bromobenzene addition compound |
| 1,2-dichloro benzene | 2,4,7-trinitro fluorenone | 2,4,7-trinitro fluorenone, 1,2-dichloro-benzene addition compound |
| 2-chloromethyl benzene | 2,4,7-trinitro fluorenone | 2,4,7-trinitro fluorenone, 2-chloromethyl-benzene addition compound |
| 2-methyl pentane | thiourea | thiourea-2-methyl pentane addition compound |
| 3-methyl pentane | thiourea | thiourea-3-methyl pentane addition compound |
| 2,2'-dimethyl pentane | thiourea | thiourea-2'2'-dimethylpentane adduct |
| 2,3-dimethyl pentane | thiourea | thiourea-2'3'-dimethylpentane adduct |
| n-hexane | thiourea | thiourea-n-hexane adduct |
| benzene | picric acid | benzene picrate |
| toluene | picric acid | toluene picrate |
| xylene (o, m, p) | picric acid | xylene (o, m, p) picrate |

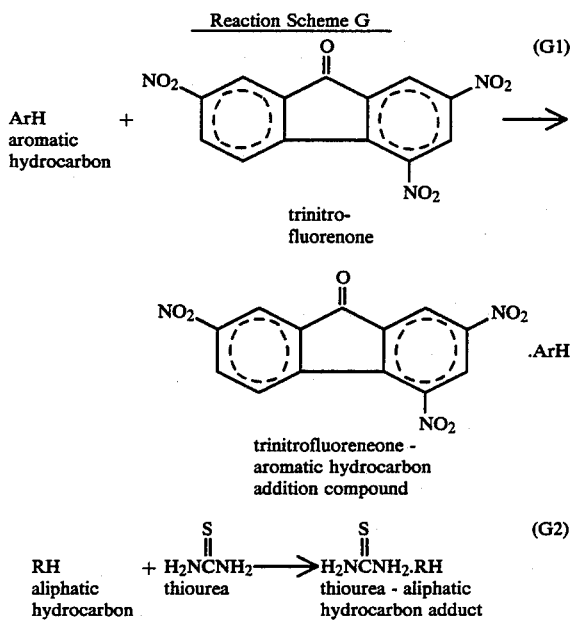

Reaction Scheme G trinitrofluorenone trinitrofluoreneone - aromatic hydrocarbon addition compound RH + H₂NCNH₂ ⟶ H₂NCNH₂·RH     (G2)
aliphatic   thiourea    thiourea - aliphatic
hydrocarbon            hydrocarbon adduct An illustrative, non-exhaustive listing of analytes within this class is provided by Table XIX. Each analyte identified is a hydrocarbon; and in each instance, it is the entirety of the chemical composition and molecular structure as a whole which serves as the identifying reactive entity indicative of this specific class. The selective derivatizing agents suitable for controlled reaction with each member of this specific chemical class are provided by Table XVIII. Two types are listed: nitrophenols and nitroquinones useful in preparing sensitized films for the detection of aromatic hydrocarbons; and thioureas useful in preparing sensitized films for detecting aliphatic hydrocarbons. Preferred examples of each type of selective derivatizing agent are provided by Tables XVIII and XIX respectively.

The combination with an aromatic or aliphatic hydrocarbon analyte of interest with one of the selective derivatizing agents is described by Reaction Scheme H. Reaction H1 illustrates the reaction and reaction product provided by an aromatic hydrocarbon and a preferred nitroquinone. Similarly, Reaction H2 illustrates the reaction and reaction product of an aliphatic hydrocarbon with a preferred thiourea. In each instance, the reaction product is formed in-situ as a plurality of immobilized nucleating sites on the surface of the exposed sensitized film for hydrocarbons. In each instance also, the composition of the individual nucleating sites is solely that of the reaction product formed by the selective derivatizing agent and an individual hydrocarbon analyte of interest representative of this chemical class.

Subsequent to the formation of the immobilized nucleating sites on the surface on the solid substrate, a metastable supersaturated developer solution is provided for treatment of the individual nucleating sites such that a plurality of optically detectable crystals are formed. The substance comprising the developer solution is preferably identical to the reaction product formed by the selective derivatizing agent and the individual hydrocarbon analyte of interest in the sample. Alternatively, the composition of the developer solution comprises a substance which is at least an analogue of the reaction product formed by the derivatizing agent and the hydrocarbon analyte, the degree of similarity and analogy (or homology) varying with the nature of the individual analyte to be detected In each instance, however, the treating of the immobilized nucleating sites with the developer solution yields a plurality of light scattering crystals whose optical detection serves as a qualitative and/or quantitative measure of the individual analyte of interest in the sample.

INORGANIC CHEMICAL CLASSES AND ANALYTES

The chemical classes described hereinafter each lie within the Order of inorganic substances and include the families of atomic elements physically present as neutral molecules; and atomic elements and radical groups in ionized form. It will be recognized and understood that detection by the assay methodology of the present invention most often, but now always, relies on the inorganic analyte of interest to be present in an ionized state, a cation or anion, in order to be detected. It is presumed that the ionic state can be achieved following conventionally accepted procedures of mixing the analyte with aqueous and/or non-aqueous fluids comprising liquids or gases; and that while the analyte of interest may initially be in compounded form, they will upon mixing with a suitable gas or liquid become ionized into a charged anionic or cationic state. In most instances, however, it is expected that the inorganic analyte of interest will be ionized using liquids.

Chemical Class AA': Alkali Metal Cations And Ammonium

This specific chemical class is limited in chemical composition and structure to five alkali metals—sodium, potassium, lithium, cesium, rubidium—and ammonium. The composition of each member therefore serves as the identifying reactive entity which identifies the inorganic analyte of interest to be detected as being of this chemical class. The source of the cation in solution is itself immaterial in view of the many different ways and manners by which such alkali metals may be compounded as chemical compositions. Most typical are ionic salts which upon addition to a liquid medium yields the cation ion in detectable form.

The assay method of the present invention employed for the detection of alkali metal cations and ammonium is described by the information provided by Table XX and Reaction Scheme AA' respectively.

TABLE XX

| ALKALI METALS TO BE DETECTED | PREFERRED DERIVATIZING AGENT | PREFERRED DEVELOPER SOLUTION |
|---|---|---|
| sodium (Na+) | zinc uranyl acetate | sodium zinc uranyl acetate |
| potassium (K+) | sodium tetraphenyl boron | potassium tetraphenyl borate |
| lithium (Li+) | ferric periodate | lithium ferric periodate |
| cesium (Cs+) | sodium tetraphenyl boron | cesium tetraphenyl borate |
| ammonium (NH₄+) | sodiun tetraphenyl boron | ammonium tetraphenyl borate |
| rubidium (Rb+) | sodium tetraphenyl boron | rubidium tetraphenyl borate |

Reaction Scheme AA'

Na+ + [ZnH(UO₂)₃][CH₃COO]₉ ⟶     (AA'1)
sodium ion  zinc uranyl acetate

-continued
Reaction Scheme AA'

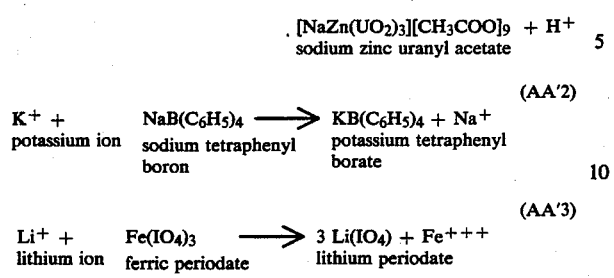

The preferred derivatizing agent selective for alkali metal cations indicated within Table XX. The nature of the reaction and the reaction product is described by Reactions AA'1, AA'2, and AA'3. In each instance, the reaction product is formed in-situ as a plurality of immobilized nucleating sites on the exposed sensitized film for alkali metals.

Subsequent to the formation of the nucleating sites, the reaction product material is treated with a metastable supersaturated developer solution comprising a substance which is at least an analogue of the reaction product yielded by the individual alkali metal analyte and the derivatizing agent. Preferably, the developer solution is identical to the reaction product comprising the immobilized nucleating site material, as is indicated within Table XX. Alternatively, however, compositions analogous to the material forming the nucleating sites may be employed so long as a plurality of optical detectable crystals are formed. In this manner, one may optically detect and measure the presence of alkalli metal cations in a quantitative or qualitative manner.

Chemical Class BB': Alkaline Earth Metal Cations

This specific chemical class detectable by the present assay methodology comprises alkaline earth metal cations, divalent metallic ions, including magnesium ions, calcium ions, strontium ions, and barium ions. Each member of this specific chemical class is an atomic element whose atomic nature and structure serves as the identifying reactive entity by which to distinguish the analyte from other inorganic substances at large. It is expected that the alkaline earth metal analyte of interest to be detected will be initially present in compounded form, most typically a salt, which after dissolution in an appropriate liquid medium provides the individual alkaline earth metal in a cationic state. Accordingly, all compositions which can be physically altered to provide an alkaline earth metal in an ionized state are within the scope of the present assay methodology.

Details of the preferred assay methodology are provided by Table XXI and Reaction Scheme BB' respectively.

TABLE XXI

| ALKALINE EARTH METAL IONS TO BE DETECTED | PREFERRED DERIVATIZING AGENT | PREFERRED DEVELOPER SOLUTION |
|---|---|---|
| magnesium ($Mg^{++}$) | potassium oxalate | magnesium oxalate |
| calcium ($Ca^{++}$) | sodium oxalate | calcium oxalate |
| strontium ($Sr^{++}$) | sodium rhodizonate | strontium rhodizonate |
| barium ($Ba^{++}$) | sodium rhodizonate | barium rhodizonate |

Reaction Scheme BB'

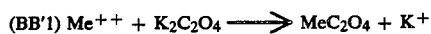

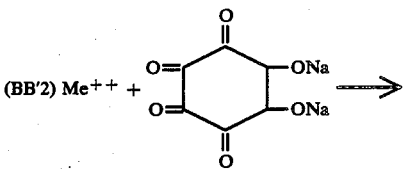

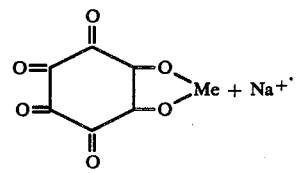

Wherein $Me^{++}$ is an alkaline earth metal ion.

The derivatizing agents selectively reactive with divalent alkaline earth metals are alkali methoxalate and sodium rhodizonate. The preferred derivatizing agents are identified by Table XXI. Similarly, Reactions BB'1 and BB'2 identify the nature of the reaction and the individual reaction products yielded by the preferred derivatizing agents with individual alkaline earth metal cations. In each instance, the reaction product material is formed in-situ as a plurality of immobilized nucleating sites on the exposed sensitized film for alkali earth metals. After the nucleating sites have been formed, they are treated with a metastable supersaturated developer solution such that a plurality of detectable light scattering crystals are formed. The developer solution preferably comprises a substance which is chemically identical to the reaction product formed by the derivatizing agent with the alkaline earth metal cation of interest. Alternatively, the developer solution may comprise a substance which is merely an analogue or homologue of the reaction product material comprising the immobilized nucleating sites. Nevertheless, so long as the treatment with the developer solution yields detectable crystals, the specific chemical composition and structure of the substance comprising the developer solution may be varied in substantial degree within these stated limits. In each instance, however, the treatment of the immobilized nucleating sites with the developer solution will yield a plurality of light scattering crystals which are optically detectable as a quantitative or qualitative measure of the alkaline earth metal ion of interest.

Chemical Class CC': Noble Metal Cations

The specific class of noble metal cations is another individual chemical class whose membership is identifiable and distinguishable based upon their atomic element nature and structure. The membership of the noble metal class includes silver ions, mercury ions, platinum ions, palladium ions, and gold ions. Each member of this class is an atomic element whose ionized structure serves as the identifying reactive entity indicative of this specific chemical class; this distinguishes each member of the class from other inorganic substances. The noble metal ions detectable by the present assay methodology exist in a variety of different cationic states—that is, having different ionic valancies. It is expected that the individual noble metal ion to be detected will initially be obtained in a compounded state such as a salt; it will therefore require dissolution in a liquid carrier to obtain the analyte of interest in an ionized form. Accordingly, all compositions able to yield an individual nobel metal in ionized form for detection are within the scope of the present invention.

The assay methodology for detection of nobel metal ions is described by Table XXII and Reaction Scheme CC' respectively.

TABLE XXII

| NOBLE METALS IONS TO BE DETECTED | PREFERRED DERIVATIZING AGENT | PREFERRED DEVELOPER SOLUTION |
|---|---|---|
| silver ($Ag^+$) | potassium iodide | silver iodide |
| mercury ($Hg^{++}$) | potassium iodide | mercuric iodide |
| platinum ($Pt^{++++}$) | potassium iodide | platinum iodide |
| palladium ($Pd^{++}$) | sodium rhodizonate | barium rhodizonate |
| gold ($Au^{+++}$) | p-dimethylamino-benzilidene rhodanine | gold salt of p-dimethyl-aminobenzilidene rhodanine |

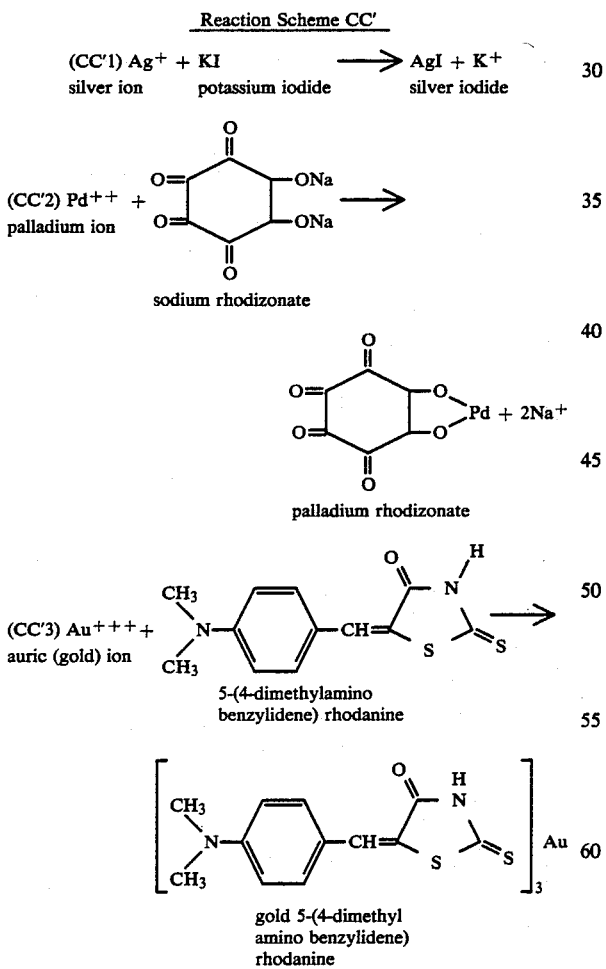

The derivatizing agents selectively reactive with individual noble metal ions comprises metal halide salts and substituted rhodamines preferably prepared as sensitized films. Preferred examples of the selective derivatizing agents are provided by Table XXII. Moreover, Reactions CC'1, CC'2, and CC'3 respectively illustrate the nature of the reaction and the reaction products yielded by these preferred derivatizing agents when combined with noble metal cations. In each instance, the reaction product of the selective derivatizing agent and the individual noble metal cation of interest forms a plurality of immobilized nucleating sites in-situ on the surface of the exposed sensitized film for noble metals. After the immobilized nucleating sites have been formed, they are treated with a metastable supersaturated solution which preferably comprises a substance which is chemically identical with the reaction product of the selective derivatizing agent and the individual noble metal cation. Alternatively, the developer solution can comprise a substance which is at least an analogue of the reaction product yielded by the derivatizing agent and the nobel metal ion analyte. In each instance, the effect of combining the developer solution with the material comprising the immobilized nucleating sties yields a plurality of light-scattering crystals which are detectable as a quantitative or qualitative measure of the noble metal cation of interest.

Chemical Class DD': Transition Metal Ions

The transition metal ions are a specific chemical class whose membership includes tin ions, lead ions, copper ions, zinc ions, cadmium ions, as well as several others. The members of this chemical class are each atomic elements which are individually identifiable by their atomic nature and structure. This serves as the identifying reactive entity for the class and distinguishes the members of this specific class from other inorganic substances. All the members of this class share common physical and chemical characteristics which have traditionally isolated them as being "transition metals."

It is required that the individual analyte to be detected be present in ionized form when the assay methodology is performed. It is also expected that these transition metals will initially be obtained in a compounded state; and will therefore require their being dissolved in a suitable liquid prior to performing the assay methodology. Specific details of the detection methodology are provided by Table XXIII and Reaction Scheme DD' respectively.

TABLE XXIII

| TRANSITION METAL IONS TO BE DETECTED | PREFERRED DERIVATIZING AGENT | PREFERRED DEVELOPER SOLUTION |
|---|---|---|
| stannous tin ($Sn^{++}$) | potassium oxalate | stannous oxalate |
| lead ($Pb^{++}$) | potassium chromate | lead chromate |
| cupric copper ($Cu^{++}$) | potassium tungstate | copper tungstate |
| zinc ($Zn^{++}$) | salicylaldoxome | zinc salicyldoxime |
| cadium ($Cd^{++}$) | sodium tungstate | cadium tungstate |

Reaction Scheme DD'

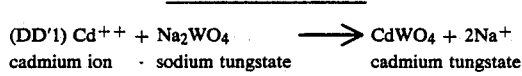

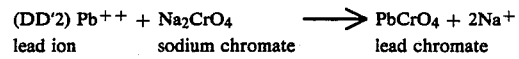

-continued
Reaction Scheme DD'

(DD'3) $Sn^{++} + 2KC_2O_4 \longrightarrow Sn(C_2O_4)_2 + 2K^+$
tin (stannous) ion | potassium oxalate | stannous oxalate (DD'4) $Zn^{++}$ + 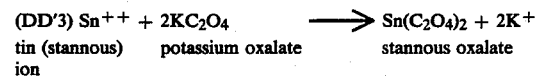
zinc ion
salicylaldoxime

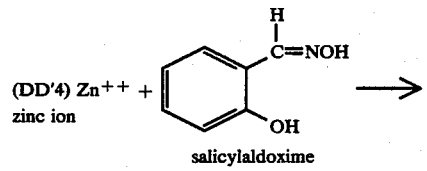 $+ 2H^+$ zinc salicylaldoxime

The derivatizing agents selectively reactive with individual transition metal ions comprise alkali methtungstates, chromates, oxalates, and substituted alkyl aldoximes suitable for preparing sensitized films. Preferred examples of the selective derivatizing agents are listed within Table XXV. Similarly, Reactions DD'1, DD'2, DD'3, and DD'4 illustrate the nature of the reactions and of the reaction products for these preferred derivatizing agents when combined with a transition metal ion of interest. In each instance, the reaction product material is formed in-situ as a plurality of immobilized nucleating sites on the surface of the exposed sensitized film for transition metals. After the immobilized nucleating sites have been formed, they are treated with a metastable supersaturated developer solution which is preferably identical with the reaction product yielded by the chosen derivatizing agent and the individual transition metal ion of interest. Alternatively, the developer solution may comprise a substance which is merely an analogue or homologue of the reaction product provided by the derivatizing agent and the analyte. In each instance, the combination of the developer solution with the immobilized nucleating sites yields a plurality of light scattering crystals which are optically detectable and serve as a qualitative and/or quantitative measure of the transition metal ion of interest.

Chemical Class EE': Inorganic Halide Anions

The inorganic chemical class specifically detected are halides whose membership includes fluoride ions, chloride ions, bromide ions, and iodide ions. Each of these are ionized atoms in solution whose chemical nature and structure as an atomic element identifies it as being within this inorganic chemical class. By its limited membership and its specific atomic composition and structure, each member of this chemical class can be identified and distinguished from any other inorganic element or molecule.

Halide anions can be individually detected by selective derivatizing agents which are metallic nitrates. Preferred examples of these derivatizing agents which are selectively reactive with halide ions are provided by Table XXIV and Reaction Scheme EE' respectively.

TABLE XXIV

| INORGANIC HALIDE ION TO BE DETECTED | PREFERRED DERIVATIZING AGENT | PREFERRED DEVELOPER SOLUTION |
|---|---|---|
| $Fl^-$ | silver nitrate | silver fluoride |
| $Cl^-$ | silver nitrate | silver chloride |
| $Br^-$ | mercuric nitrate | mercuric bromide |
| $I^-$ | lead nitrate | lead iodide |

Reaction Scheme EE'

$2 X^- + Ag(NO_3)_2 \longrightarrow AgX + 2 NO_3^-$ (EE'1)
silver nitrate — silver halide $2 X^- + Pb(NO_3)_2 \longrightarrow PbX_2 + 2 NO_3^-$ (EE'2)
lead nitrate — lead halide $2 X^- + Hg(NO_3)_2 \longrightarrow Hg(X)_2 + 2 NO_3^-$ (EE'3)
mercuric nitrate — mercuric halide wherein $X^-$ = halide ion = chloride ion; fluoride ion; bromide ion; iodide ion.

Regardless of which metallic nitrate is preferred for use as the selective derivatizing agent, a reaction product is formed in-situ as a plurality of immobilized nucleating sites on the surface of the exposed sensitized film for halides. Reactions EE'1, EE'2, and EE'3 individually illustrate the nature of the reaction and the reaction product formed in-situ as immobilized nucleating sites. Subsequent to their formation, the nucleating sites are treated with a metastable supersaturated developer solution comprising a substance which is at least an analogue of the reaction product yielded by the derivatizing agent and the individual halide anion which is the analyte of interest. Most preferred for use as the developer solution are substances which are identical with the reaction product forming the immobilized nucleating sites themselves. Alternatively, analogues or homologues of the material forming the nucleating sites may be employed as the developer solution so long as a plurality of optically detectable crystals are formed. In each instance, the treating of the immobilized nucleating sites with the developer solution yields light-scattering crystals which are detectable and serve as a measure of the halide anion of interest in either a quantitative or qualitative manner.

Chemical Class FF': Halogens

This inorganic chemical class of halogens is specifically detected as neutral molecules, usually in gaseous form. The membership includes fluorine, chlorine, bromine, and iodine. Each of these are diatomic compositions whose chemical form and structure identifies them as being within this specific inorganic chemical class. By its limited membership and its specific composition and structure, each member within this specific chemical class can be identified and distinguished from the halide anions or any other inorganic element or molecule.

Molecular halogens can be individually detected by selective derivatizing agents which are alkenes such as unsaturated dicarboxylic acids. Preferred examples of these derivatizing agents which are selectively reactive with molecular halogens are provided by Table XXV and Reaction Scheme FF' respectively.

TABLE XXV

| HALOGEN TO BE DETECTED | PREFERRED DERIVATIZING AGENT | PREFERRED DEVELOPER SOLUTION |
|---|---|---|
| fluorine (Fl$_2$) | maleic acid | 2,3-diflourosuccinic acid |
| chlorine (Cl$_2$) | fumaric acid | 2,3-dichlorosuccinic acid |
| bromine (Br$_2$) | fumaric acid | 2,3-dibromosuccinic acid |
| iodine (I$_2$) | maleic acid | 2,3-diiodosuccinic acid |

Reaction Scheme FF'

(FF'1) Cl$_2$ + chlorine

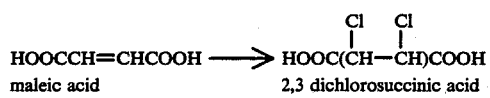

HOOCCH=CHCOOH ⟶ HOOC(CH—CH)COOH
maleic acid                2,3 dichlorosuccinic acid (FF'2) Br$_2$ + bromine

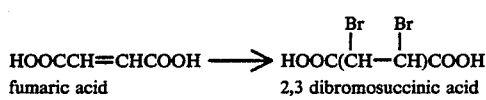

HOOCCH=CHCOOH ⟶ HOOC(CH—CH)COOH
fumaric acid              2,3 dibromosuccinic acid Regardless of which alkene or unsaturated dicarboxylic acid is preferred for use as the selective derivatizing agent, a reaction product is formed in-situ as a plurality of immobiized nucleating sites on the surface of the exposed sensitized film for halogens. Reactions FF'1 and FF'2 individually illustrate the nature of the reaction and the reaction product material formed in-situ as immobilized nucleating sites. Subsequent to their formation, the nucleating sites are treated with a metastable supersaturated developer solution comprising a substance which is at least an analogue of the reaction product yielded by the derivatizing agent and the molecular halogen which is the analyte of interest. Most preferred for use as the developer solution are substances which are identical with the reaction product material forming the immobilized nucleating sites themselves. Alternatively, analogues (or homologues) in varying degree of the material forming the nucleating sites may be employed as the developer solution—so long as a plurality of optically detectable crystals are formed. In each instance, the treating of the immobilized nucleating sites with the developer solution yields light scattering crystals which are optically detectable and serve as a measure of the molecular halogen of interest in either a quantitative or qualitative manner.

Chemical Class GG': Sulfur Anions

The chemical class specifically detectable by the present invention comprises sulfur anions and sulfur containing radical anions in varying oxidative states. The membership of this specific chemical class is thus limited to sulfide anions and ionized moieties of sulfur and oxygen in varying ratios and oxidative states. Clearly, therefore, the composition and structure of the class membership serves as the identifying reactive entity which distinguishes them from any other inorganic substance.

The assay method for detection of sulfur anions and oxidized sulfur radical anions disclosed by Table XXVI and Reaction Scheme GG' respectively.

TABLE XXVI

| SULFUR IONS AND SULFUR CONTAINING RADICALS TO BE DETECTED | PREFERRED DERIVATIZING AGENT | PREFERRED DEVELOPER SOLUTION |
|---|---|---|
| sulfate ion (SO$_4$=) | barium nitrate | barium sulfate |
| sulfite ion (SO$_3$=) | copper nitrate | copper sulfite |
| sulfide ion (S=) | lead nitrate | lead sulfide |

Reaction Scheme GG'

(GG'1) $SO_4^= + Ba(NO_3)_2 \longrightarrow Ba(SO_4)_2 + 2 NO_3^-$
sulfate ion   barium nitrate         barium sulfate (GG'2) $SO_3^= + Cu(NO_3)_2 \longrightarrow Cu(SO_3)_2 + 2 NO_3^-$
sulfate ion   cupric nitrate         cupric sulfite (GG'3) $S^= + Pb(NO_3)_2 \longrightarrow PbS + 2NO_3^-$
sulfate ion   lead nitrate           lead sulfide The derivatizing agent selectively reactive with sulfide ions and sulfur containing radicals comprises metallic nitrates. The preferred derivatizing agents are identified within Table XXVI and reacts in accordance with Reactions GG'1, GG'2, and GG'3 respectively to yield a reaction product formed in-situ as a plurality of immobilized, nucleating sites on the surface of the exposed sensitized film for sulfur anions. Clearly, the material forming the reaction product of the nucleating sites will vary with the exact identity, composition, and structure of the individual analyte; and the individual reaction products yielded via Reaction Scheme GG' are individually different and distinct from one another. After the formation of immobilized nucleating sites, they are treated with a metastable supersaturated developer solution comprising a substance which preferably is identical to the reaction product yielded by the derivatizing agent and the sulfide anion or sulfur containing radical anion of interest. Alternatively, however, a substance which is an analogue of the reaction product forming the individual nucleating sites may also be usefully employed. In each instance, the combination of developer solution with the immobilized nucleating sites provides a plurality of light scattering, optically detectable crystals which serve as a measure of the sulfide anion or the sulfur containing radical anion of interest in a quantitative or qualitative manner.

Chemical Class HH': Phosphorous Radical Anions

The class specifically detectable by the present invention comprises phosphorus containing radicals in varying oxidative states. The membership of this specific chemical class includes ionized molecules of phosphorous and oxygen of varying ratios and oxidative states. Clearly therefore, the composition and structure of the membership as anionic radicals comprising phosphorous and oxygen serves as the identifying reactive entity which distinguishes them from any other inorganic substance.

The assay method for detection of phosphorous containing radical anions is disclosed by Table XXVII and Reaction Scheme HH' respectively.

TABLE XXVII

| PHOSPHOROUS CONTAINING RADICALS TO BE DETECTED | PREFERRED DERIVATIZING AGENT | PREFERRED DEVELOPER SOLUTION |
|---|---|---|
| metaphosphate | calcium nitrate | calcium metaphoshate |
| tribasic phosphate (ortho) | calcium nitrate | calcium (ortho) phosphate |

Reaction Scheme HH'

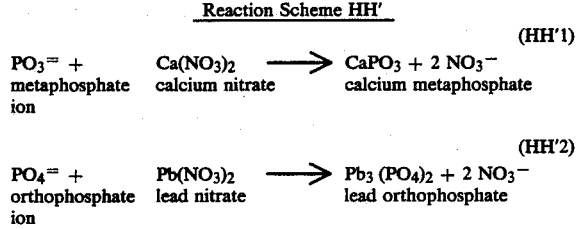

(HH'1) $PO_3^= +$ $Ca(NO_3)_2$ $\longrightarrow$ $CaPO_3 + 2 NO_3^-$
metaphosphate ion    calcium nitrate    calcium metaphosphate (HH'2) $PO_4^= +$ $Pb(NO_3)_2$ $\longrightarrow$ $Pb_3(PO_4)_2 + 2 NO_3^-$
orthophosphate ion    lead nitrate    lead orthophosphate The derivatizing agent selectively reactive phosphorous radical anions comprises metallic nitrates. The preferred derivatizing agents are identified within Table XXVII; and react in accordance with Reactions HH'1 and HH'2 respectively to yield a reaction product formed in-situ as a plurality of immobilized nucleating sites on the surface of the exposed sensitive film for phosphorous anions. Clearly, the material forming the reaction product of the nucleating sites will vary with the exact composition and structure of the individual anionic analyte; and the individual reaction products yielded via Reactions HH'1 and HH'2 are individually different and distinct from one another. After the formation of immobilized nucleating sites, these sites are treated with a metastable supersaturated developer solution comprising a substance which preferably is identical to the reaction product yielded by the derivatizing agent and the phosphorous radical anion of interest. Alternatively, however, a substance which is an analogue or homologue of the reaction product forming the individual nucleating sites may also be usefully employed. In each instance, the combination of developer solution with the immobilized nucleating sites provides a plurality of light scattering, optically detectable, crystals which serve as a measure of the phosphorous radical of interest in a quantitative or qualitative manner.

The present invention is not to be restricted in form nor limited in scope except by the claims appended hereto.

What I claim is:

1. An assay method for selectively detecting an organic analyte of interest which is neither an aldehyde nor a ketone and has not been converted into either an aldehyde or a ketone, said method comprising the steps of:
   obtaining a fluid believed to contain the organic analyte of interest, said organic analyte being devoid of reactive carbonyl groups and comprising at least one identifying reactive entity whose chemical composition and structure identifies the organic analyte as being of a specific chemical class;
   exposing the organic analyte of interest in said fluid to a derivatizing agent selectively reactive with with said identifying reactive entity of said organic analyte such that a reaction product is formed in-situ as a plurality of immobilized, nucleating sites;
   treating said immobilized, nucleating sites with a metastable supersaturated solution comprising a substance which is at least an analogue of the reaction product yielded by said derivatizing agent and said organic analyte such that a plurality of detectable crystals are formed; and
   detecting the presence of said formed crystals as a measure of the organic analyte of interest in the fluid.

2. The assay method as recited in claim 1 wherein said identifying chemical entity comprises a nitrogeneous base.

3. The assay method as recited in claim 2 wherein said organic analyte of interest is selected from the group consisting of primary amines, secondary amines, tertiary amines, hydrazines hydrazides, polyamines, ammonia, hydrazine, hydroxylamine and hydroxylamines.

4. The assay method as recited in claim 1 wherein said identifying reactive entity comprises a sulfur moiety and the organic analyte of interest is selected from the group consisting of mercaptans and thiophenols.

5. The assay method as recited in claim 1 wherein said identifying reactive entity is a halogen moiety and the organic analyte of interest is an alkyl halide.

6. The assay method as recited in claim 1 wherein said identifying reactive entity is a hydroxyl group and the analyte of interest is an alcohol.

7. The assay method as recited in claim 1 wherein said identifying reactive entity is a hydroxyl group and the organic analyte of interest is a phenol.

8. The assay method as recited in claim 6 or 7 wherein a plurality of hydroxyl groups are present and the organic analyte of interest is a polyol.

9. The assay method as recited in claim 1 wherein said identifying reactive entity is at least one carboxylic acid group and the organic analyte of interest is an organic acid.

10. The assay method as recited in claim 1 wherein said identifying reactive entity is at least one sulfonylic acid group and the organic analyte of interest is a sulfonic acid.

11. The assay method as recited in claim 1 wherein said identifying chemical entity is a hydrocarbon and said organic analyte of interest is selected from the group consisting of saturated and unsaturated aromatic and aliphatic compositions.

12. An assay method for selectively detecting an inorganic analyte of interest which has not been converted into being part of either an aldehyde or a ketone composition, said method comprising the steps of:
   obtaining a fluid believed to contain the inorganic analyte of interest, said inorganic analyte comprising an identifying reactive entity whose chemical composition and structure identifies the inorganic analyte as being of a specific chemical class;
   exposing the inorganic analyte of interest in said fluid to a derivatizing agent selectively reactive with with said identifying reactive entity of said inorganic analyte such that a reaction product is formed in-situ as a plurality of immobilized, nucleating sites;
   treating said immobilized, nucleating sites with a metastable supersaturated solution comprising a substance which is at least an analogue of the reaction product yielded by said derivatizing agent and said inorganic analyte such that a plurality of detectable crystals are formed; and detecting the presence of said formed crystals as a measure of the inorganic analyte of interest in the fluid.

13. The assay method as recited in claim 12 wherein said reactive entity is the inorganic analyte of interest is an alkali metal cation.

14. The assay method as recited in claim 12 wherein said reactive entity and said analyte is a cation selected from the group consisting of alkaline earth metal cations.

15. The assay method as recited in claim 12 wherein said reactive entity and said analyte is a cation selected from the group consisting of noble metal cations.

16. The assay method as recited in claim 12 wherein said reactive entity and said analyte is a cation selected from the group consisting of transition metals.

17. The assay method as recited in claim 12 wherein said identifying reactive entity and said analyte is an anion selected from the group consisting of halide anions.

18. The assay method as recited in claim 12 wherein said identifying reactive entity and said analyte is selected from the group consisting of molecular halogens.

19. The assay method as recited in claim 12 wherein said identifying reactive entity is selected from the group consisting of sulfides, sulfites, and sulfates and said analyte is a sulfur anion.

20. The assay method as recited in claim 12 wherein said identifying reactive entity and said analyte comprises a phosphorous radical anion.

* * * * *